(12) United States Patent
Liang

(10) Patent No.: US 9,181,292 B2
(45) Date of Patent: Nov. 10, 2015

(54) METHODS FOR PREPARATION OF GLYCOSPHINGOLIPIDS AND USES THEREOF

(76) Inventor: Pi-Hui Liang, Taipei (TW)

( * ) Notice: Subject to any disclaimer, the term of this patent is extended or adjusted under 35 U.S.C. 154(b) by 0 days.

(21) Appl. No.: 13/344,557

(22) Filed: Jan. 5, 2012

(65) Prior Publication Data

US 2012/0178705 A1    Jul. 12, 2012

Related U.S. Application Data

(60) Provisional application No. 61/430,117, filed on Jan. 5, 2011.

(51) Int. Cl.
| | | |
|---|---|---|
| *C07H 15/18* | (2006.01) | |
| *C07H 1/00* | (2006.01) | |
| *C07H 15/06* | (2006.01) | |
| *A61K 39/39* | (2006.01) | |
| *C07H 15/04* | (2006.01) | |

(52) U.S. Cl.
CPC .............. *C07H 15/06* (2013.01); *A61K 39/39* (2013.01); *C07H 1/00* (2013.01); *C07H 15/04* (2013.01); *C07H 15/18* (2013.01)

(58) Field of Classification Search
None
See application file for complete search history.

(56) References Cited

U.S. PATENT DOCUMENTS

| 7,928,077 B2 | 4/2011 | Wong |
| 2007/0238871 A1 | 10/2007 | Tsuji |
| 2008/0260774 A1 | 10/2008 | Wong |
| 2009/0233875 A1 | 9/2009 | Tsuji |

FOREIGN PATENT DOCUMENTS

| CN | 1405172 A | 3/2003 |
| CN | 101012254 A | 8/2007 |
| JP | 64-056693 A | 3/1989 |
| WO | WO 2008/128062 A1 | 10/2008 |

OTHER PUBLICATIONS

Lin, K.-H. et al., Antimicrobial Agents and Chemotherapy, "In Vivo Protection Provided by a Synthetic New Alpha-Galactosyl Ceramide Analog against Bacterial and Viral Infections in Murine Models", Oct. 2010, vol. 54, No. 10, p. 4129-4136.*
Trappeniers, M. et al., ChemMedChem, "Synthesis and in vitro Evaluation of alpha-GalCer Epimers", 2008, vol. 3, pp. 1061-1070.*
Plettenberg, O., et al. J. Org. Chem, 2002, 67:4559-4564.
Koeman, F.A.W., Tetrahedron, 1993, 49(24):5292-5304.
Chinese Office Action issued Dec. 23, 2014 in connection with Chinese Application No. 201280011839.4.
International Search Report and Written Opinion mailed Nov. 7, 2012 in connection with PCT/US2012/020388.
International Preliminary Report on Patentability mailed Jul. 18, 2013 in connection with PCT/US2012/020388.

* cited by examiner

*Primary Examiner* — Shaojia Anna Jiang
*Assistant Examiner* — Bahar Craigo
(74) *Attorney, Agent, or Firm* — Wolf, Greenfield & Sacks, P.C.

(57) ABSTRACT

Methods for synthesis and preparation of alpha-glycosphingolipids are provided. Methods for synthesis of α-galactosyl ceramide, and pharmaceutically active analogs and variants thereof are provided. Novel alpha-glycosphingolipids are provided, wherein the compounds are immunogenic compounds which serve as ligands for NKT (natural killer T) cells.

5 Claims, 9 Drawing Sheets

METHODS FOR PREPARATION OF GLYCOSPHINGOLIPIDS AND USES THEREOF

CROSS-REFERENCE TO RELATED APPLICATIONS

This application claims the priority of U.S. Provisional Patent Application Ser. No. 61/430,117 filed Jan. 5, 2011 entitled "METHODS FOR PREPARATION OF GLYCOSPHINGOLIPIDS AND USES THEREOF" which is incorporated by reference herein.

TECHNICAL FIELD OF THE INVENTION

This present invention relates to novel glycosphingolipid analogues, intermediates for the production thereof. In particular, the invention relates to novel processes for the preparation of glycosphingolipids. More particularly, the invention relates to methods for synthesis and uses of novel alpha-linked glycospingolipid compounds.

BACKGROUND OF THE INVENTION

Studies show NKT cells, a unique lymphocyte subpopulation, are characterized by the coexpression of an invariant antigen receptor and NK receptors. Human NKT cells (Vα24-Jα18) are activated by a specific glycolipid antigen, in a CD1d-dependent manner. CD1d molecules are heterodimers, composed of a heavy polypeptide chain non-covalently associated with a 2-microglobulin, and have substantial structural similarity to major histocompatibility complex (MHC) class I proteins. After activation, NKT cells exhibit MHC-independent antitumor activity against tumor cells in vitro and in vivo through several mechanisms. Activated Vα24 NKT cells produce a high level of cytokines, such as IFN-γ, thereby bridging innate and adaptive immunity through the activation of other effector cells including dendritic cells (DC), NK cells, and CD8$^+$ T cells. NKTs play a regulatory role in the immune system, thus they are attractive targets for immunotherapy.

At present, the most well studied CD1d-presented antigen is alpha-galactosylceramide (αGalCer, KRN-7000). It initially drew interest when extracts derived from the marine sponge, *Agelas mauritianus*, demonstrated novel anti-tumor properties. Kirin Beer pharmaceutical company (U.S. Pat. No. 5,849,716). This potent activity was later traced to a family of alpha-linked glycospingolipids (GSLs), from which αGalCer was structurally optimized. The GSLs consists of a sugar moiety alpha-linked to a ceramide which is formed by an amide bond of a fatty acid with a long chain base.

Upon activation by αGalCer, NKT cells release proinflammatory (Th1) and immunomodulatory (Th2) cytokine. The production of $T_H1$ cytokines is thought to correlate with antitumor, antiviral/antibacterial, and adjuvant activities, whereas $T_H2$ cytokine production is thought to subdue autoimmune diseases. αGalCer has been the subject of clinical trials for its anti-cancer potential, but it was terminated during phase I. The non-specific nature of the cytokine profile induced by αGalCer, both Th1 and Th2, makes it less effective as a therapeutic treatment. This interpretation has encouraged many groups to focus on the searching for compounds which increase the selectivity toward either the $T_H1$ or $T_H2$ cytokines response. Wong et al. have synthesized a series of glycolipids bearing aromatic groups on the acyl side chain and found these molecules to skew the cytokine release profile towards a $T_H1$ response (J. Am. Chem. Soc. 2006, 128, 9022-9023. US 2007/0238871). In vivo experiment on mice with aggressive lung cancer tumors (TC1 cell line) and breast cancer tumors (4T1 cell line) have showed that the lung cancer-bearing mice treated with the new glycolipids had significantly prolonged survival time compared to those treated with αGalCer. In breast cancer-bearing mice, treatment with the new glycolipids inhibited the tumor growth rate by 75% of untreated group, as compared to 50% inhibition in mice treated with α-GalCer (Proc. Natl. Acad. Sci. U.S.A. 2007, 104, 10299-10304).

Therefore, there is a need for efficient means for synthesis of alpha-glycosphingolipids, such as αGalCer compounds, as well as a need for synthesis of novel alpha-glycosphingolipid compounds with immunomodulatory effects.

SUMMARY OF THE INVENTION

The present invention provides novel methods for synthesizing galactosylsphingolipids, including novel compounds related to α-galactosyl ceramides and active analogs thereof, such as C34.

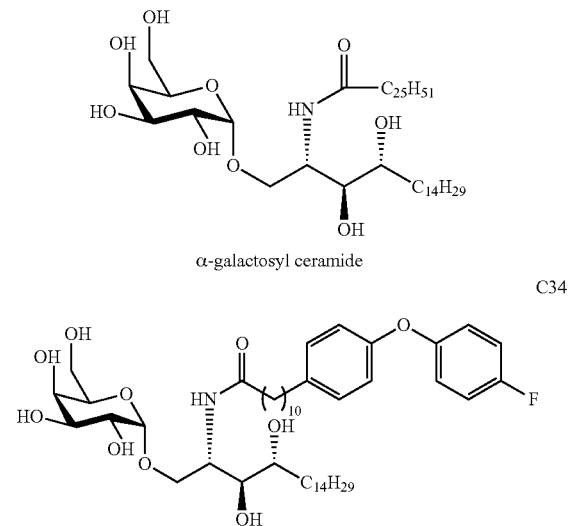

α-galactosyl ceramide

C34

The invention provides, in one embodiment, a compound represented by the structure of formula (1):

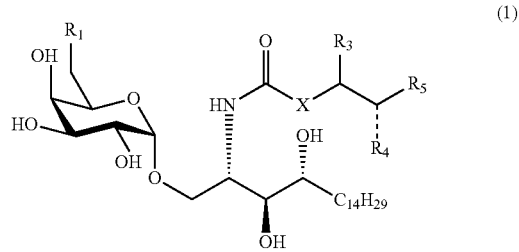

(1)

wherein $R_1$=OH, NH$_2$, NHCOR$_2$; $R_2$=H or an alkyl, alkenyl, or alkyl terminating in aryl, substituted aryl, heteroaryl, or substituted heteroaryl; X=alkyl group, alkenyl; $R_3$, $R_4$=H, OH; $R_5$=aryl, substituted aryl, heteroaryl, or substituted heteroaryl.

In one embodiment of the invention, the compound of formula 1 may be obtained by a process that includes, inter alia, the step of removing the benzylidene protecting group and hydrogenating of the compound represented by the structure of formula (2):

(2)

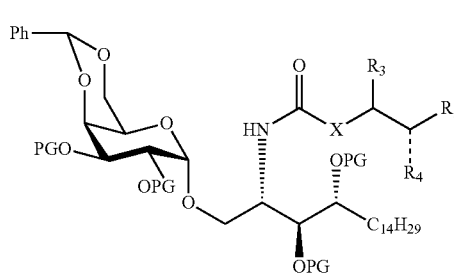

where PG is a hydroxyl protecting group.

In another embodiment, the hydroxyl protecting group may be benzyl.

In one embodiment of the invention, the compound of formula 2 where $X=(CH_2)_8$, $R_3=H$, $R_4=H$, $R_5=$4-F-phenoxy-phenyl, may be obtained by a process which includes, inter alia, the step of amide bond formation between compounds of formula (3) and formula (4).

(3)

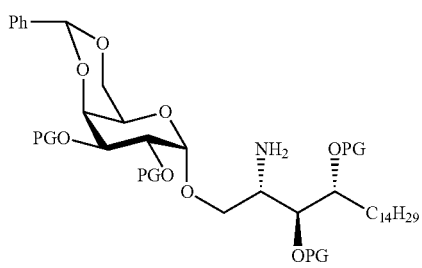

where, in one embodiment, PG is benzyl (4)

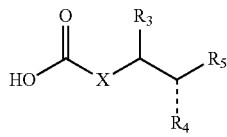

where in one embodiment, X=alkyl group, alkenyl, $R_3=H$, OH, $R_4=H$, OH, $R_5=$aryl, substituted aryl, heteroaryl, or substituted heteroaryl.

In one embodiment of the invention, the compound of formula (3), wherein R is benzyl, may be obtained by a process that includes, inter alia, the step of: reducing the azide group of a compound represented by the structure of formula (5):

(5)

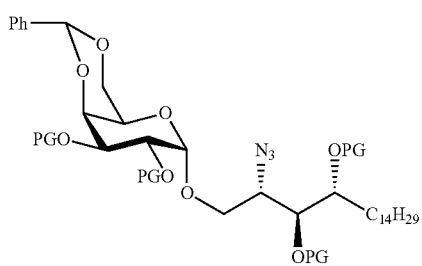

In one embodiment of the invention, the compound of formula 5, wherein PG is benzyl, may be obtained by a process including, inter alia, the step of: reacting a compound represented by the structure of formula (6)

(6)

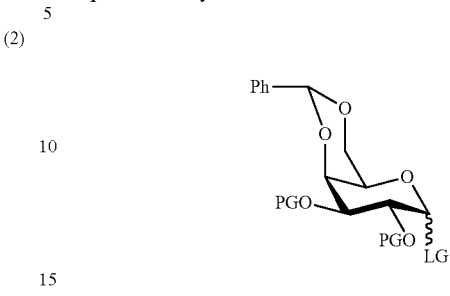

wherein PG is a hydroxyl protecting group and LG is a leaving group, with a compound represented by the structure of formula (7)

(7)

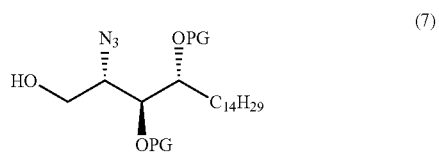

wherein PG is a hydroxyl protecting group, to form an alpha glycosidic bond, thus obtaining the compound of formula (5). In another embodiment, the leaving group of formula (6) may be any one of:

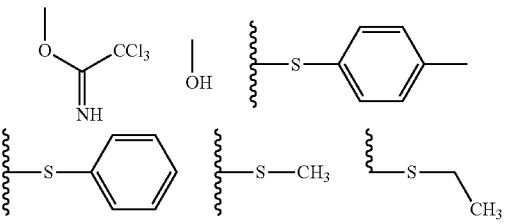

In one embodiment of the invention, the compound of formula 1 may be obtained by a process that includes, inter alia, the step of removing the benzylidene protecting group and hydrogenating of the compound represented by the structure of formula (8):

(8)

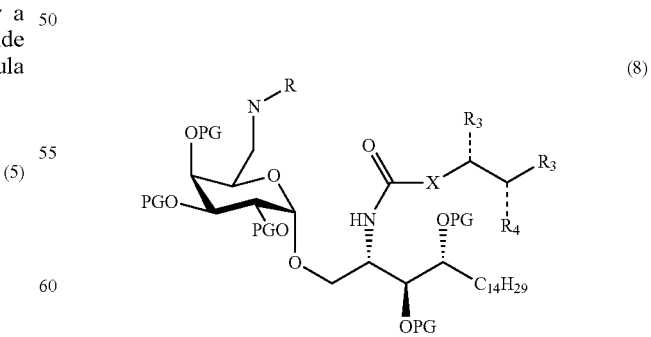

wherein PG is hydroxyl protective group. In another embodiment, the PG may be, inter alia, benzyl.

In one embodiment of the invention, the compound of formula (8) may be obtained by a process including, inter alia, the step of: reacting a compound represented by the structure of formula (9) with a compound represented by alkanoic acid, aryl acid, aryl-alkanoic acid, substituted aryl-alkanoic acid, and heterocyclic acid.

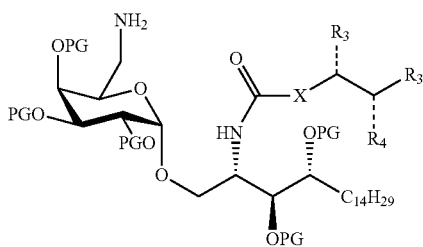

(9)

wherein PG is a hydroxyl protecting group.

In one embodiment of the invention, the compound (9) may be obtained from the process including, inter alia, the step of: reducing the azide of a compound represented by the structure of formula (10)

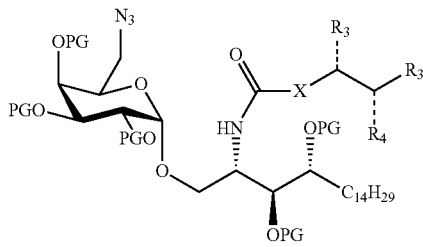

(10)

where PG is hydroxyl protective group.

In one embodiment of the invention, the compound (10) may be obtained from the process including, inter alia, the step of: substituting of a compound represented by the structure if formula (11)

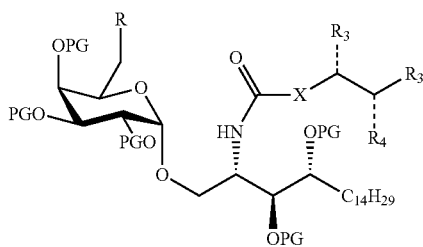

(11)

where R is leaving group, thereby obtaining the compound of formula (11).

In another embodiment, the R may be, inter alia, methanesulfonyl or toluenesulfonyl. In one embodiment of the invention, the compound of formula (11) may be obtained by a process including, inter alia, the step of: conducting a substitution of the hydroxyl moiety of the compound represented by the structure of formula (12)

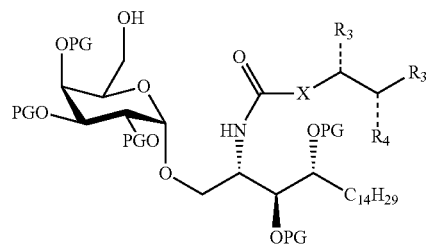

(12)

In another embodiment, the substitution may be conducted in the presence of base and methanesulfonyl chloride or toluenesulfonyl chloride.

In one embodiment of the invention, the compound (12) may be obtained from the process including, inter alia, the step of: hydrolysis of the compound represented by the structure of formula (13)

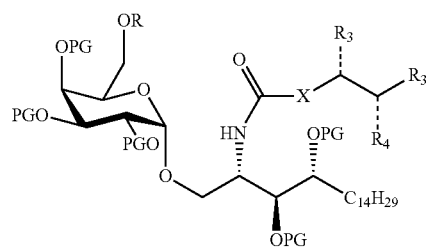

(13)

where R is hydroxyl protective group, in one embodiment, R is alkyl ester. In another embodiment, R is acetate.

In one embodiment of the invention, the compound (13) may be obtained from the process including, inter alia, the step of: amide bond formation of the compound represented by the structure of formula (14),

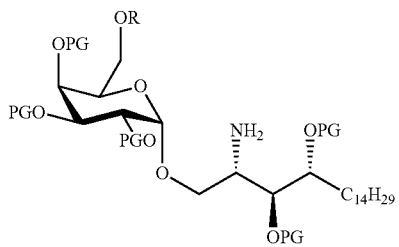

(14)

and the compound represented by the structure of formula (4).

In one embodiment of the invention, the compound (14) may be obtained from the process including, inter alia, the step of: reducing the azide of a compound represented by the structure of formula (15).

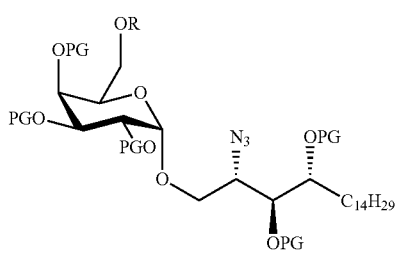

(15)

In one embodiment of the invention, the compound (15) may be obtained from the process including, inter alia, the step of: reacting a compound represented by the structure of formula (16)

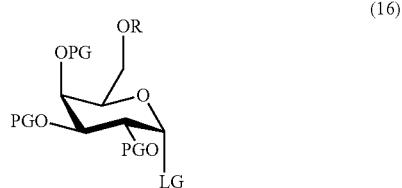

(16)

wherein PG is a hydroxyl protecting group, LG is a leaving group, and R is ester, with a compound represented by the structure of formula (7), wherein PG is a hydroxyl protecting group, to form an alpha glycosidic bond, thus obtaining the compound of formula (15).

In another embodiment, the leaving group may be any one of:

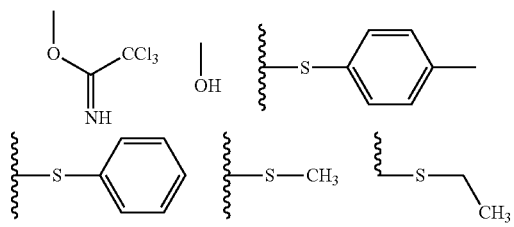

In one embodiment of the invention, the compound of formula (17) may be obtained by the process including, inter alia, the step of: removing the hydroxyl protecting group PG1, thereby obtaining the compound of formula (17), the PG1 may be, inter alia, trityl.

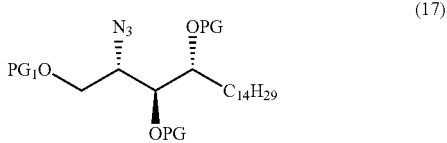

(17)

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The novel methods of the synthesis of formula (1) in general comprise binding the ceramide with saccharide, but it is also possible to first bond with the phytosphingosine and then to derive the amino group into the amide group to complete the formula 1.

Figure 1:
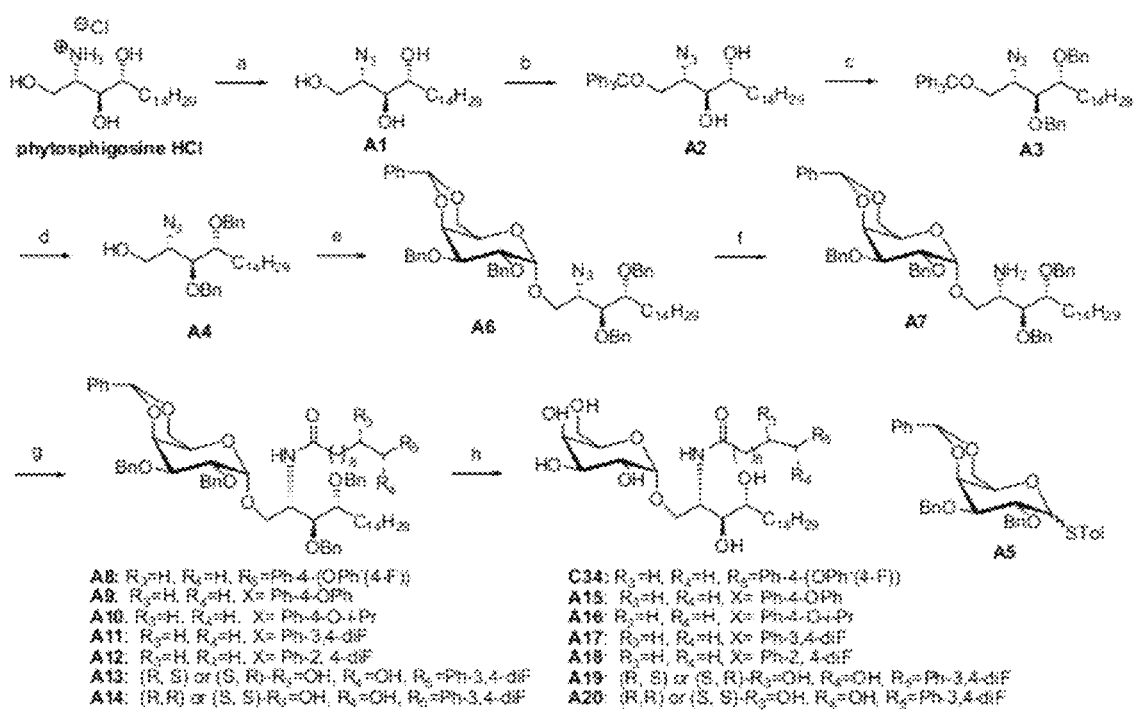
FIG. 1 is a schematic illustration depicting synthesis of C34, A15-21. Scheme 1. Reagents and conditions: (a) TfN$_3$, K$_2$CO$_3$, CuSO$_4$, DCM, MeOH, H$_2$O; (b) trityl chloride, triethylamine, toluene; (c) benzyl chloride (BnCl), NaH, DMF, Toluene; (d) HCl, toluene, MeOH; (e) A5, Me$_2$S$_2$-Tf$_2$O, THF, 4 Å MS; (f) LiAlH$_4$, THF; (g) RCO$_2$H, HBTU, NMM, DCM; (h) Pd(OH)$_2$, H$_2$, MeOH, DCM.
Figure 2:
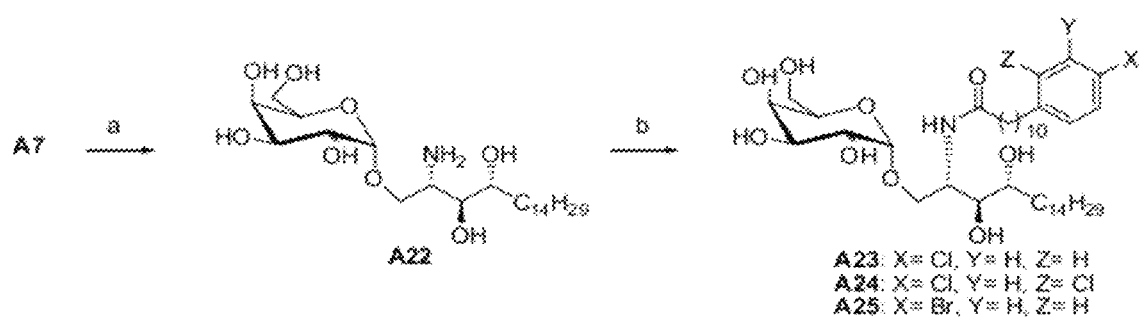
FIG. 2 is a schematic illustration depicting synthesis of compound A23-A25. Scheme 2. Reagents and conditions: (a) Pd(OH)$_2$, H$_2$ (80 psi), MeOH, DCM, AcOH; (b) RCO$_2$H, HBTU, NMM, DCM MeOH.
Figure 3:
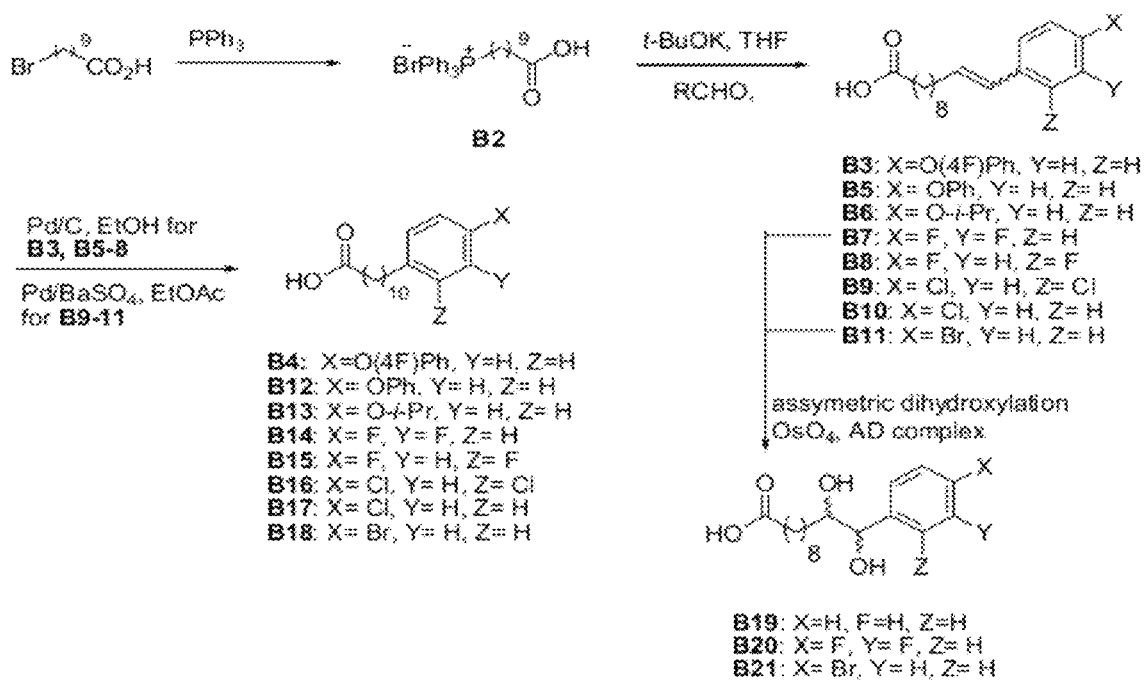
FIG. 3 is a schematic illustration depicting synthesis of formula (4). Scheme 3.

As an example of such synthesis, it is also possible to synthesize the compound represented by formula (1) where galactose C6' is hydroxyl group via the following steps (see FIG. 1-3).

Phytosphingosine hydrochloride ((2S,3S,4R)-2-amino-1, 3,4-octadecanetriol) is a starting material, although there are several methods as described in Curr. Org. Chem. 2002, 6, 365-391 for the synthesis of phytosphingosine. The commercial source—phytosphingosine hydrochloride is prepared from the appropriate yeast fermentation broth which can be obtained a reasonable price in large quantities (Evonik Degussa Taiwan Ltd.). The isomeric sphingosines having a configuration different from that of the natural sphingosine can be prepared according to the methods described in Helvetica Chimica Acta 1957, 470, 1145; or Chem. Commun. 1991, 820.

In the first step, the amino group of phytosphingosine was converted to an azido group by a diazo transfer reaction by fresh prepared $TfN_3$ to afford A1. The preparation of $TfN_3$ can be found in Tetrahedron Lett 1996, 37, 6029-6032. Trityl protection of primary alcohol A1 gave crude A2 which was directly subjected to benzylation conditions of NaH and BnCl to afford compound A3. In the present route, while benzyl group is employed as the protective group of the hydroxyl group, other appropriate groups such as benzoate, (p-methoxy)-benzyl, or isopropylidene may also be used. Toluene was selected as the solvent to synthesize compounds from A1 to A3. The benzylation reaction of second alcohols failed to proceed in toluene as sole solvent. To overcome the low reactivity of the benzylation in toluene, a co-solvent system of 10% DMF in toluene was employed to improve the solubility of NaH and intermediate alkoxide. After aqueous workup, crude A3 was obtained as a solution in toluene and subjected to acidic deprotection to give glycosyl acceptor A4. Various acid can be used in the trityl group deprotection, such as hydrochloride, sulfuric acid, hydrogen bromide, trifluoroacetic acid, $BF_3.OEt$, nitric acid, acidic resin (e.g. Amberlite IR120®) and so on.

Previously, various glycosylation methods have been applied in glycolipids syntheses, including glycosyl fluoride, glycosyl trichloroacetoimidate, glycosyl bromide and glycosyl iodide[20-23]. Tetrahedron 1998, 54, 3141-3150; J Org Chem 2005, 70, 10260-10270; J Org Chem 2002, 67, 4559-4564; Chem Commun 2007, 2336-2338. The glycosyl imidate has been initially employed in our synthesis with excellent yield (89%) and anomeric selectivity ($\alpha/\beta=9/1$). Due to the imidate being easily hydrolyzed and usually needed to be prepared fresh, using this leaving group for glycosylation in the large-scale synthesis might encounter storage and purification problems. Alternatively, thioglycoside A5 as a donor can be achieved using Lewis acid, such as TMSOTf, $Tf_2O$, $BF_3.OEt_2$, TfOH, $Me_2S_2$-$Tf_2O$ as catalysts and using molecular sieves to de-hydrate. Compound A5 contains azido group which favors glycosylation, while the amino group of phytosphingosine is protected by amide or carbamate (t-butyl carbamate) as seen in U.S. Pat. No. 5,849,716; US 2007/0238871; J. Am. Chem. Soc. 2004, 126, 13602-13603; J. Org. Chem. 2005, 70, 10260-10270; Tetrahedron 1998, 54, 3141-3150; Synthesis 2004, 847-850; Bioorg. Med. Chem. Lett. 2006, 16, 2195-2199. The 2-NH and 1-OH may form a intramolecular hydrogen bonding which hampers it as a nucleophile to attack the activated glycoside and results in low yields in glycosylation. After the glycosylation between A4 and A5, column purification can afford A6 both in pure α-form, and pure β-form.

Compound A6 which contain azido group can be reduced by using any of lithium aluminium hydride, sodium borohydride, a borane complex, phospine complex, enzyme reduction, hydrogenation, or transfer hydrogenation. Instead of using phospine complex which generates side product-phosphine oxide which is difficult to remove, the reduction of azide by lithium aluminium hydride ($LiAlH_4$) gave higher purity amine A7. Compound A7 was coupled with various prepared carboxylic acids (see FIG. 3 for the preparative methods) to give corresponding amide compounds. Global deprotection of these compounds was achieved under hydrogenolysis conditions in the presence of catalytic $Pd(OH)_2$ and $H_2$ in mix solvents of MeOH and $CH_2Cl_2$ to yield analogues of C34, compounds A15-21.

The reductive dehalogenation of aryl halides on acyl chain is carried out by the hydrogenation reaction of the chloro- and bromo-acyl containing compounds. Therefore, to avoid dehalogenation reaction, A6 was deprotected and reduced by hydrogenesis in the presence of catalytic $Pd(OH)_2$ and $H_2$. After that resulting amine A22 was coupled with appropriate acids (see FIG. 3 for the preparation methods) in the coupling conditions, analogues A23-25 were yielded (FIG. 2). For this process many methods of reaction are known, particularly for amidation. It is also possible to use acyl chloride, and acid anhydride or a carboxylic acid. The carboxylic acid is used in a condensation reaction in the presence of an appropriate condensing agent. The appropriate condensing agent used in the reaction includes dicyclohexylcarbodiimide (DCC), 1-ethyl-3-(3' dimethylaminopropyl)carbodiimine (EDC), as well as 2-(1H-benzotriazole-1-yl)-1,1,3,3-tetramethyluronium hexafluoro-phosphate (HBTU), hydroxybenzotrazole (HOBt) or the like. In order to progress rapidly the reaction, an organic base such as triethylamine, pyridine, N-methylmorpholine, dimethylaniline, 4-dimethylaminopyridine, N-methylpiperidine, N-methylpyrrolidine is added. The solvent may be any one inert solvents which will not be involved in the reaction such as tetrahydrofuran, ethyl ether, toluene, chloroform, methylene chloride, ethyl acetate, acetone or the like.

For the preparation of various substituted phenylalkanoic acids, the Wittig reaction is employed as can be seen in FIG. 3. In this process, the ω-bromo-alkanoic acids are mixed with triphenyl phosphine in the presence of the solvent. The reaction is generally carried out with an appropriate solvent, but when the reaction is low, it can be increased by performing the reaction in the absence of a solvent. The solvent may be any of inert solvents which will not be involved in the reaction, e.g. toluene, benzene, diglyme, dimethyl sulfide or the like.

Figure 4:
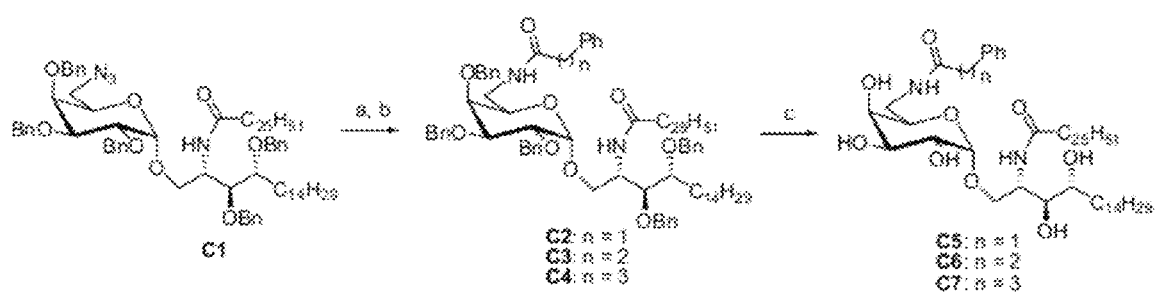
FIG. 4 is schematic illustration depicting synthesis of compounds C5-C7. Scheme 4. Reagents and conditions: (a) PPh$_3$, THF, H$_2$O; (b) Ph(CH$_2$)$_n$CO$_2$H, HBTU, NMM, DCM; (c) Pd(OH)$_2$, H$_2$, DCM, MeOH.
Figure 5:
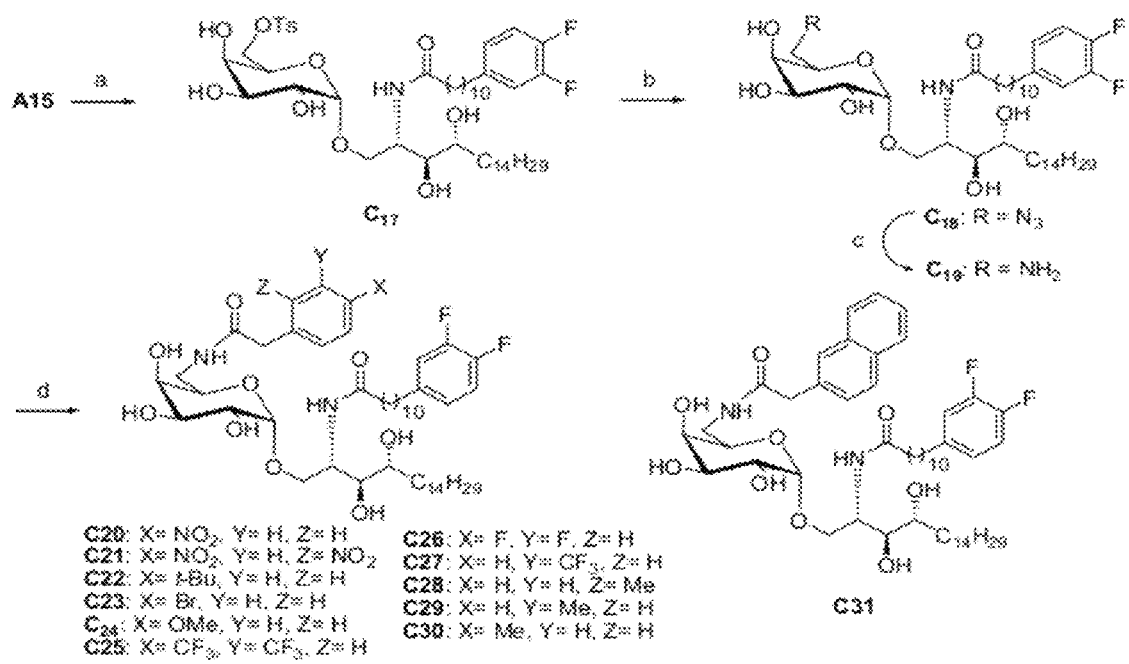
FIG. 5 is schematic illustration depicting synthesis of compounds C20-C31. Scheme 5. Reagents and conditions: (a) TsCl, pyridine; (b) NaN$_3$, DMF; (c) PPh$_3$, THF, H$_2$O; (d) RCH$_2$CO$_2$H, HBTU, NMM, MeOH, DCM.

As another example of the synthesis, it is also possible to synthesize the compound represented by the formula (1) by carrying out various substitutions at galactose C6' position via the following steps (see FIG. 4-5).

The synthesis of C6 modified analogues began with compound C1 as described in Org Lett 2002, 4, 1267-1270. Reduction of azide, then amidation with different commercial aromatic acids and fully deprotection yielded C5-C6 (FIG. 4, Scheme 4). In addition, to avoid a tedious protective group interconversion for the preparation from compound C1, a different strategy was employed in the synthesis of C6" and acyl chain bi-modified compounds (FIG. 5). The C6" hydroxyl group of A15 can be tosylated or mesylated by toluene sulfonyl chloride or methane sulfonyl chloride in the presence of base, such as pyridine, dimethylpyridine, triethylamine, diethylpropylamine, DBU or the like, and then the corresponding tosylate or mesylate group can be substituted with azide by sodium azide to give C18. Staudinger reduction of azide, amidation with variety of acids yielded C20-31.

Use of the Compound of the Present Invention

The compounds represented by the formula (1) exhibit the following physiological activities, can be used as immunotherapeutic agent against cancers or as immunostimulating agent against the other diseases.

APC activating activity: IL-2 secretions can be measured in the A20CD1d and mNK1.2 cells system as APC and effector cells as shown in Example 2.

Immunostimulating activity: IFN-γ and Il-4 Cytokine secretions can be measured as shown in Example 2 which female C57BL/6 mouse (16w4d) was sacrificed and spleen was harvested for the assay.

Anti-tumor agent: The compound of the present invention has Th1 biased cytokine secretion profile and can be used an antitumor activity and an immunostimulating effect.

While the compounds in current invention can be used as the immunotherapeutic agent against tumor they may be used alone or combined with chemotherapy or radiotherapy.

The compounds of the present invention as anti-tumor agents or immunostimulating agent may be administered in any appropriate dosage routes. The compound is generally formed into a preparation which is in the form of diluted and formed with a pharmaceutically acceptable carrier (liposome, or micelle). When the compound of present invention is used, it can be administrated orally or parent rally to human or mammalian. For example, the compounds of present invention when used as injection, they can be administered intravenously, intramuscularly, subcutaneously or inhalation in a form such as solution, suspension or emulsion with appropriate solvent. In this case, polysorbatesm or macrogol, cholesterol can be added as a solubilizing agent, if necessary. When the compounds in the present invention are administered orally, they can be in a form of tablet, powder, granule, or dry syrup into an appropriate additive.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

The synthetic method and physicochemical properties of the compounds of the present invention are described below (referring to the number of compounds in the process of synthesis, see the reaction schemes as shown in FIG. 1-FIG. 5).

In the schemes shown herein, the following abbreviations are used:
THF: tetrahydrofuran
DMF: N,N-dimethyl formide
MS-4A: Molecule Sieves-4A (dehydrating agent)
$CH_2Cl_2$: dichloromethane
NMM: N-methyl morpholine
HBTU: O-benzotriazole-N,N,N',N'-tetramethyl-uronium-hexafluoro-phosphate
TMSOTf: trimethylsilyl trifluoromethansulfonate
$Tf_2O$: trifluoromethansulfonic anhydride
$CDCl_3$: d1-chloroform
NMR: nuclear magnetic resonance
HRMS: high resolution mass
ESI: electron spray ionization The other abbreviations have the same meanings as those in the schemes shown above.

Synthetic Scheme 1 (FIG. 1)

The routes show specifically the process for preparing the compound C34, A13, A14, A15, A16, A18, A19, A20, A21 and the compounds according to the present invention) can also be synthesized in accordance with this process.

Synthesis of (2S,3S,4R)-2-azido-D-ribo-octadecane-1,3,4-triol (A1)

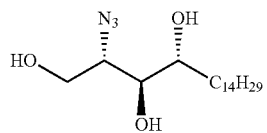

To the solution of sodium azide (64.3 g, 989 mmol) in 250 mL water was added dichloromethane (350 mL). The biphasic mixture was cooled to 5° C. in an ice bath and triflic anhydride (47.5 mL, 283 mmol) was added over a 20 min period, keeping the temperature under 10° C. After stirring for 2.5 h in an ice bath, the reaction mixture was quenched with 70 mL sat. $K_2CO_3$. The organic phase was isolated and the aqueous phase was extracted with $CH_2Cl_2$ (200 mL). The organic phases were combined to afford triflyl azide solution in dichloromethane. [Caution! Triflyl azide is explosive, needed to be stored with solvent.]

To a solution of cupric sulfate (0.35 g, 1.4 mmol) in water (150 mL) was added phytosphingosine hydrochloride (highly pure form of phytosphingosine hydrochloride [(2S,3S,4R)-2-amino-1,3,4-octadecanetriol] from the appropriate yeast fermentation broth is commercial available for a reasonable price in large quantities, 50.0 g, 141 mmol), potassium carbonate (29.28 g, 211.9 mmol) and methanol (1.0 L). The suspension was cooled to 0-5° C. in a salt ice bath and the triflyl azide solution (in 550 mL $CH_2Cl_2$) was added over a 10 min period. After stirring the reaction mixture for 12 h at rt, the mixture was concentrated. The residue was slurried in water (1.0 L) and stirred at room temperature for 12 h. The precipitate was filtered and washed with water (500 mL×2). The residue was dried by azeotropic distillation (70-80° C., 200-250 mmHg) with toluene (1.5 L) to afford (2S,3S,4R)-2-azido-D-ribo-octadecane-1,3,4-triol (A1) (47.0 g, 137 mmol, 97%) as off-white solids. mp: 87° C. $^1$H-NMR ($CD_3OD$, 400 MHz) δ 3.85 (dd, J=11.6, 3.3 Hz, 1H), 3.69 (dd, J=11.6, 7.9 Hz, 1H), 3.50-3.55 (m, 1H), 3.43-3.47 (m, 2H), 1.22-1.60 (m, 26H), 0.83 (t, J=6.4 Hz, 3H). $^{13}$C-NMR ($CD_3OD$, 100 MHz) δ 74.6, 71.5, 65.3, 61.2, 32.5, 31.7, 29.4, 29.4, 29.1, 25.4, 22.4, 13.1. HRMS (ESI) calculated for $C_{18}H_{37}N_3O_3Na$ [M+Na]$^+$: 366.2733, found: 366.2729.

Synthesis of (2S,3S,4R)-2-azido-3,4-di-O-benzyl-D-ribo-octadecan-1,3,4-triol (A4)

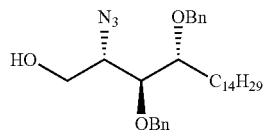

To the mixture of (2S,3S,4R)-2-azido-D-ribo-octadecane-1,3,4-triol (47.0 g, 137 mmol) in toluene (1.0 L) was added triethylamine (46 mL, 332 mmol) and trityl chloride (42.0 g, 151 mmol). After stirring at 50-55° C. for 6 h, triethylamine (4.6 mL, 33 mmol) and triphenylmethyl chloride (4.20 g, 15.1 mmol) were added and then stirred for an additional 15 h. Water (1.0 L) was added and the mixture was stirred for 3 min. The organic phase was washed with water (1.0 L, 500 mL) and concentrated to afford crude (2S,3S,4R)-2-azido-1-trityl-D-ribo-octadecan-1,3,4-triol (A2). The analytical sample for NMR was purified by column chromatography. $^1$H-NMR (CDCl$_3$, 400 MHz) δ 7.22-7.47 (m, 15H), 3.62 (dd, J=3.7, 10.1 Hz, 2H), 3.53 (m, 2H), 3.40 (dd, J=6, 10.1 Hz, 1H), 2.35 (brs, 1H), 1.83 (brs, 1H), 1.20-1.52 (m, 26H), 0.87 (t, J=6.8 Hz, 3H). $^{13}$C-NMR (CDCl$_3$, 100 MHz) δ 143.35, 128.54, 128.01, 127.27, 87.78, 74.19, 72.18, 63.48, 62.31, 31.90, 31.74, 29.67, 29.64, 29.60, 29.55, 29.34, 25.59, 22.67, 14.10.

To the solution of crude (2S,3S,4R)-2-azido-1-trityl-D-ribo-octadecan-1,3,4-triol (A2) in toluene (750 mL) and DMF (75 mL) was added sodium hydride (60% in mineral oil, 21.9 g, 548 mmol) in three portions over a 10 min period. The mixture was stirred for 30 min after which benzyl chloride (50.5 mL, 0.438 mmol) was added to the reaction mixture. The mixture was warmed to 50-60° C. and stirred for 18 h. The mixture was then cooled to 0° C. and water (50 mL) was added dropwise. The organic phase was washed with sat. ammonium chloride (500 mL×2) and water (500 mL×2). The organic phase was filtered through Celite pad and the filtrate was concentrated to afford crude (2S,3S,4R)-2-azido-2,3-di-benzyl-1-trityl-D-ribo-octadecan-1,3,4-triol (A3).

To the solution of A3 in toluene/methanol (600 mL, 1/1) was added aqueous HCl (33%, 6.0 mL). The mixture was warmed to 50-60° C. and stirred for 20 h. The reaction mixture was quenched with 1.0 N NaOH (55 mL) and concentrated. The residue was partitioned with toluene (500 mL) and water (500 mL). The organic phase was concentrated and the residue was purified by column chromatography (crude 100 g, silica gel 500 g, ethyl acetate/n-hexane=1/10) to afford (2S,3S,4R)-2-azido-2,3-di-benzyl-D-ribo-octadecan-1,3,4-triol (A4) (27.5 g, 52.5 mmol, 38% over 4 steps) as yellow oil. $^1$H-NMR (CDCl$_3$, 200 MHz) δ 7.26-7.39 (m, 10H), 4.69 (d, J=1.4 Hz, 2H), 4.59 (d, J=4.3 Hz, 2H), 3.59-3.94 (m, 5H), 1.26-1.61 (m, 26H), 0.88 (t, J=6.4 Hz, 3H). $^{13}$C-NMR (CDCl$_3$, 50 MHz) δ 137.9, 137.6, 128.5, 128.4, 128.1, 127.97, 127.81, 127.10, 80.38, 78.96, 73.59, 72.49, 63.03, 62.20, 21.90, 30.16, 29.66, 29.35, 25.43, 22.67, 14.11. HRMS (ESI) calculated for C$_{32}$H$_{49}$N$_3$O$_3$Na [M+Na]$^+$: 546.3672, found: 546.3689

Synthesis of 4-methylphenyl 2,3-O-dibenzyl-4,6-O-benzylidene-1-thiol-D-galactopyranoside (A5)

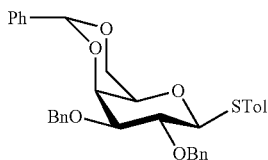

Compound A5 may be prepared according to the method described in Plettenburg, O. et al. *J. Org. chem.* 2002, 67, 4559-4564.

Data of compound A5: $^1$H-NMR (CDCl$_3$, 400 MHz) δ 7.58 (d, J=8.1 Hz, 1H), 7.50 (m, 2H), 7.23-7.42 (m, 15H), 6.98 (d, J=8.0 Hz, 1H), 5.46 (s, 1H), 4.69 (m, 4H), 3.54 (d, J=9.5 Hz, 1H), 4.35 (dd, J=12.3, 1.5 Hz, 1H), 4.12 (d, J=3.2 Hz, 1H), 4.03 (dd, J=9.8, 3.6 Hz, 1H), 3.82 (t, J=9.3 Hz, 1H), 3.60 (dd, J=9.2, 3.4 Hz, 1H), 3.39 (s, 1H), 2.28 (s, 3H).

Synthesis of 2-azido-3,4-di-O-benzyl-1-O-(2,3-di-O-benzyl-4,6-O-benzylidene-α-D-galactopyranosyl)-D-ribo-octadecan-1,3,4-triol (A6)

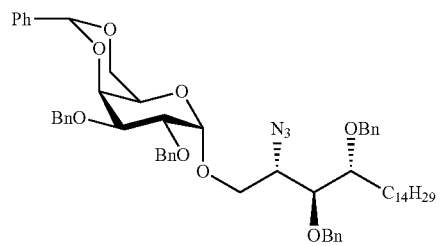

To the solution of dimethyl disulfide (10.0 mL, 113 mmol) in dichloromethane (75 mL) was added triflic anhydride (17 mL, 100 mmol) at 0-5° C. in a salt ice bath. After stirring the reaction mixture in the salt ice bath for 30 min, Me$_2$S$_2$-Tf$_2$O was obtained as a 1.0 M solution in dichloromethane and it can be stored in an ice bath for 3 hours.

Compound A4 (27.3 g, 52.2 mmol), A5 (34.7 g, 62.6 mmol) and 4 Å molecular sieve (33 g) were mixed and dried under vacuum for 1 h and THF (520 mL) was added to the mixture. The mixture was cooled to −10° C. in a salt ice bath before adding Me$_2$S$_2$-Tf$_2$O (1.0 M solution in CH$_2$Cl$_2$, 94 mL, 94 mmol). After stirring for 20 min, the reaction mixture was quenched with triethylamine (22 mL) and then diluted with dichloromethane (200 mL). The mixture was filtered through Celite and washed with dichloromethane (50 mL). The combined filtrate was concentrated and partitioned with dichloromethane (500 mL) and water (500 mL). The organic phase was concentrated and the residue was purified by column chromatography (crude weight=153 g, 600 g silica gel, ethyl acetate: n-hexane=1:15 to 1:12 to 1:10) to afford 2-azido-3,4-di-O-benzyl-1-O-(2,3-di-O-benzyl-4,6-O-benzylidene-α-D-galactopyranosyl)-D-ribo-octadecan-1,3,4-triol (A6) (32.07 g, 33.60 mmol, 64%) as off-white wax. mp: 59° C. $^1$H-NMR (CDCl$_3$, 400 MHz) δ 7.22-7.50 (m, 25H), 5.44 (s, 1H), 4.96 (d, J=3.4 Hz, 1H), 4.85 (d, J=11.9 Hz, 1H), 4.79 (d, J=12.3 Hz, 1H), 4.73 (d, J=12.3 Hz, 1H), 4.66-4.69 (m, 2H), 4.59 (d, J=8.5 Hz, 1H), 4.56 (d, J=12.8 Hz, 1H), 4.48 (d, J=11.5 Hz, 1H), 4.15 (d, J=2.8 Hz, 1H), 4.06-4.12 (m, 1H), 3.98-4.04 (m, 3H), 3.86 (dd, J=12.5, 1.5 Hz, 1H), 3.68-3.73 (m, 3H), 3.60-3.62 (m, 1H), 3.55 (s, 1H), 1.25-1.55 (m, 26H), 0.87 (t, J=7.1 Hz, 3H). $^{13}$C-NMR (CDCl$_3$, 100 MHz) δ 138.75, 138.36, 138.01, 137.82, 128.85, 128.37, 128.34, 128.26, 128.22, 128.09, 127.90, 127.79, 127.75, 127.70, 127.66, 127.61, 127.50, 127.45, 126.33, 101.05, 99.13, 79.41, 78.95, 76.68, 75.80, 75.44, 74.66, 73.77, 73.49, 72.06, 72.03, 69.31, 68.43, 62.97, 61.80, 31.91, 30.01, 29.75, 29.69, 29.67, 29.65, 29.63, 29.60, 29.35, 25.44, 22.68, 14.10. [α]$_D^{25}$ +63.1 (c 1.0, CHCl$_3$). HRMS (ESI) calculated for C$_{59}$H$_{75}$N$_3$O$_8$Na [M+Na]$^+$: 976.5452, found: 976.5483.

Synthesis of 3,4-di-O-benzyl-1-O-(2,3-di-O-benzyl-4,6-O-benzylidene-α-D-galactopyranosyl)-2-(11-(4-(4-fluorophenoxy)phenyl)undecanoyl)amino-D-ribo-octadecan-1,3,4-triol (A8)

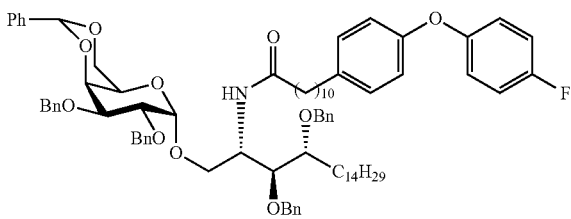

To the solution of compound A6 in THF (340 mL), lithium aluminum hydride (1.910 g, 50.33 mmol) was added in two portions to produce compound A7 (32.07 g, 33.61 mmol) and cooled in an ice bath. The mixture was returned to room temperature (rt) and stirred for 70 min. The mixture was cooled to 0° C. before subsequently quenching with water (1.9 mL), 1.0 N NaOH (3.8 mL) and water (1.9 mL). The mixture was filtered through Celite pad and washed with dichloromethane (100 mL). The filtrate was concentrated and partitioned with dichloromethane (350 mL) and water (350 mL).

11-(4-(4-Fluorophenoxy)phenyl))undecanoic acid (B4) (11.27 g, 30.26 mmol) was added to the isolated organic phase, followed by NMM (9.2 mL, 84 mmol) and HBTU (19.12 g, 50.41 mmol). After stirring at room temperature for 12 h, the mixture was filtered and washed with 50 mL CH$_2$Cl$_2$. The combined filtrate was washed with sat. ammonium chloride (400 mL) and water (400 mL). The organic phase was concentrated and purified by column chromatography (crude weight=46 g, 350 g silica gel, ethyl acetate/n-hexane=1/6 to 1/5 to 1/4) to afford A8 (36.06 g, 28.11 mmol, 84%) as off-white wax. $^1$H-NMR (CDCl$_3$, 400 MHz) δ 6.86-7.51 (m, 33H), 5.84 (d, J=8.0 Hz, 1H), 5.44 (s, 1H), 4.94 (d, J=3.5 Hz, 1H), 4.83 (d, J=11.6 Hz, 1H), 4.69-4.74 (m, 3H), 4.63 (d, J=11.6 Hz, 1H), 4.57 (d, J=11.6 Hz, 1H), 4.50 (d, J=3.9 Hz, 1H), 4.47 (d, J=3.9 Hz, 1H), 4.24-4.31 (m, 1H), 4.16 (d, J=3.1 Hz, 1H) 4.03-4.12 (m, 3H), 3.92 (dd, J=10.3, 3.6 Hz, 2H), 3.73-3.79 (m, 2H), 3.56 (s, 1H), 3.51-3.53 (m, 1H), 2.55 (t, J=7.6 Hz, 2H), 1.87-1.91 (m, 2H), 1.19-1.69 (m, 42H), 0.87 (t, J=6.6 Hz, 3H). $^{13}$C-NMR (CDCl$_3$, 100 MHz) δ 172.89, 159.76, 157.36, 155.36, 153.36, 153.33, 138.63, 138.52, 138.50, 138.38, 137.81, 137.79, 129.53, 128.84, 128.64, 128.42, 128.35, 128.31, 128.29, 128.08, 127.88, 127.80, 127.69, 127.59, 127.57, 127.55, 126.29, 120.08, 120.00, 118.31, 116.24, 116.01, 100.99, 99.59, 79.81, 79.48, 76.68, 76.14, 75.68, 74.33, 73.81, 73.28, 71.88, 71.69, 69.39, 68.13, 62.91, 60.36, 50.32, 36.69, 35.17, 31.90, 31.61, 30.24, 29.78, 29.69, 29.67, 29.65, 29.59, 29.56, 29.51, 29.42, 29.35, 29.29, 25.81, 25.68, 22.66, 14.17, 14.10. HRMS (ESI) calculated for C$_{82}$H$_{105}$FNO$_{10}$ [M+H]$^+$: 1282.7723, found: 1282.7731.

Synthesis of 1-O-(α-D-galactopyranosyl)-2-(11-(4-(4-fluorophenoxy)phenyl)undecanoyl)amino-D-ribo-octadecan-1,3,4-triol (C34)

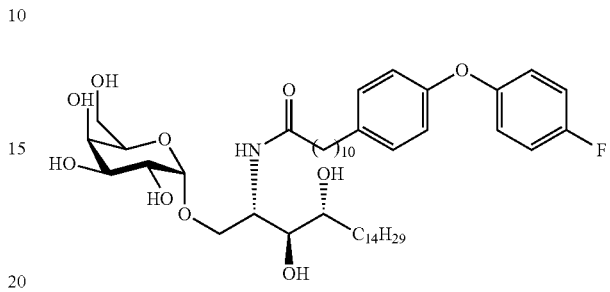

To the solution of A8 (36.06 g, 28.11 mmol) in dichloromethane/methanol (200 mL, dichloromethane/methanol=1/1) was added palladium hydroxide (1.8 g). The mixture was stirred under hydrogen (5 bar) at room temperature for 10 h. The reaction mixture was filtered through Celite pad and washed with dichloromethane/methanol (100 mL, dichloromethane/methanol=1/1). The combined filtrate was concentrated and purified by column chromatography (300 g silica gel, dichloromethane/methanol=15/1 to 10/1) to afford crude C34 (17.46 g, 20.93 mmol, purity=95.72 area % by HPLC) as off-white solids in 75% yield. Ethanol (87.5 mL) was added to the crude C34 and warmed to 50° C., acetone (87.5 mL) was then added. The solution was cooled to rt over a 3 h period and then cooled in an ice bath. The precipitate was filtered and washed with acetone (200 mL) to afford C34 (16.02 g, 19.21 mmol 68%, purity=97.15 area % by HPLC) as white solids in 92% recovery. mp: 163° C. $^1$H-NMR (CDCl$_3$/CD$_3$OD=1/1, 400 MHz) δ 7.26 (d, J=8.5 Hz, 2H), 7.07-7.17 (m, 4H), 7.00 (dd, J=6.6, 2.0 Hz, 2H), 5.03 (d, J=3.7 Hz, 1H), 4.33 (q, J=4.7 Hz, 1H), 4.05 (d, J=2.7 Hz, 1H), 4.01 (dd, J=4.6, 10.8 Hz, 1H), 3.79-3.97 (m, 6H), 3.64-3.72 (m, 2H), 2.71 (t, J=7.4 Hz, 2H), 2.34 (t, J=7.5 Hz, 2H), 1.29-1.43 (m, 42H), 1.01 (t, J=6.6 Hz, 3H). $^{13}$C-NMR (CDCl$_3$/CD$_3$OD=1/1, 100 MHz) δ 173.99, 154.82, 152.97, 137.34, 128.95, 119.39, 119.31, 117.71, 115.52, 115.29, 99.21, 73.92, 71.28, 70.41, 69.69, 69.17, 68.37, 66.63, 61.12, 49.92, 35.74, 34.50, 31.66, 31.27, 31.02, 29.10, 29.06, 28.99, 28.95, 28.88, 28.85, 28.77, 28.70, 28.60, 25.28, 25.23, 21.99, 13.10. [α]$_D^{25}$ +57.0 (c 1.0, CH$_2$Cl$_2$/CH$_3$OH: 1/1). HRMS (ESI) calculated for C$_{47}$H$_{77}$FNO$_3$ [M+H]$^+$: 834.5532, found: 834.5595.

Synthesis of 3,4-di-O-benzyl-1-O-(2,3-di-O-benzyl-4,6-O-benzylidene-α-D-galactopyranosyl)-2-(11-(4-phenoxyphenyl)undecanoyl)amino-D-ribo-octadecan-1,3,4-triol (A9)

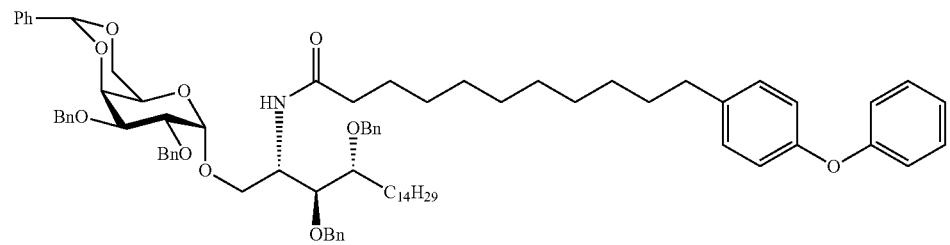

By the similar procedure of synthesis of A8, compound A6 (100 mg, 0.105 mmol) and compound B12 (33 mg, 0.093 mmol) are the starting materials to give compound A9 (45 mg, 0.036 mmol, 38%) as white wax. $^1$H-NMR (CDCl$_3$, 400 MHz) δ 7.48-7.52 (m, 2H), 7.20-7.41 (m, 25H), 7.12 (d, J=8.8 Hz, 2H), 7.06 (t, J=7.3 Hz, 1H), 6.96-7.00 (m, 2H), 6.92 (d, J=10.4 Hz, 2H), 5.83 (d, J=8.4 Hz, 1H), 5.45 (s, 1H), 4.94 (d, J=3.6, 1H), 4.84 (d, J=11.6 Hz, 1H), 4.69-4.75 (m, 3H), 4.63 (d, J=11.6 Hz, 1H), 4.57 (d, J=11.6 Hz, 1H), 4.49 (d, J=11.6 Hz, 1H), 4.48 (d, J=11.6 Hz, 1H), 4.24-4.31 (m, 1H), 4.17 (d, J=3.2 Hz, 1H) 4.03-4.12 (m, 3H), 3.87-3.96 (m, 3H), 3.74-3.80 (m, 2H), 3.56 (s, 1H), 3.50-3.56 (m, 1H), 2.57 (t, J=7.6 Hz, 2H), 1.82-1.95 (m, 2H), 1.15-1.65 (m, 42H), 0.88 (t, J=6.6 Hz, 3H). $^{13}$C-NMR (CDCl$_3$, 100 MHz) δ 172.89, 159.69, 154.86, 138.62, 138.51, 138.50, 138.38, 137.89, 137.79, 129.60, 129.49, 128.83, 128.41, 128.34, 128.31, 128.29, 128.07, 127.87, 127.82, 127.80, 127.68, 127.57, 127.55, 126.29, 122.79, 118.92, 118.41, 100.98, 99.60, 79.82, 79.48, 76.14, 75.68, 74.33, 73.80, 73.27, 71.88, 71.69, 69.38, 68.14, 62.91, 50.32, 36.70, 35.21, 31.90, 31.61, 30.24, 29.78, 29.69, 29.67, 29.65, 29.59, 29.56, 29.51, 29.41, 29.34, 29.29, 25.80, 25.68, 22.66, 14.10. HRMS (ESI) calculated for C$_{82}$H$_{106}$NO$_{10}$ [M+H]$^+$: 1264.7817, found: 1264.7834.

Synthesis of 3,4-di-O-benzyl-1-O-(2,3-di-O-benzyl-4,6-O-benzylidene-α-D-galactopyranosyl)-2-(11-(4-isopropoxyphenyl)undecanoyl)amino-D-ribo-octadecan-1,3,4-triol (A10)

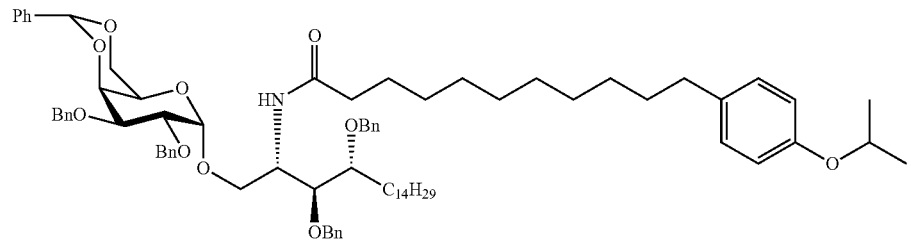

By the similar procedure of synthesis of A8, compound A6 (100 mg, 0.105 mmol) and B13 (30 mg, 0.094 mmole) were used as starting materials to afford A10 (72.0 mg, 0.059 mmol, 63%) as white wax. $^1$H-NMR (CDCl$_3$, 400 MHz) δ 7.21-7.55 (m, 25H), 7.06 (d, J=8.4 Hz, 2H), 7.78-7.84 (m, 2H), 5.86 (d, J=8.4 Hz, 1H), 5.46 (s, 1H), 4.95 (d, J=3.2, 1H), 4.85 (d, J=11.6 Hz, 1H), 4.71-4.80 (m, 3H), 4.63 (d, J=11.6 Hz, 1H), 4.58 (d, J=11.6 Hz, 1H), 4.46-4.54 (m, 3H), 4.18 (d, J=3.2 Hz, 1H), 4.05-4.14 (m, 3H), 3.88-3.97 (m, 3H), 3.75-3.82 (m, 2H), 3.58 (s, 1H), 3.51-3.57 (m, 1H), 2.53 (t, J=7.6 Hz, 2H), 1.83-1.96 (m, 2H), 1.15-1.71 (m, 48H), 0.89 (t, J=6.6 Hz, 3H). $^{13}$C-NMR (CDCl$_3$, 100 MHz) δ 172.84, 139.68, 138.60, 138.49, 138.46, 138.36, 137.77, 128.81, 128.39, 128.32, 128.28, 128.26, 128.05, 127.86, 127.79, 127.78, 127.66, 127.54, 126.26, 124.00, 116.89, 116.72, 100.96, 99.54, 79.75, 79.46, 76.10, 75.66, 74.29, 73.79, 73.25, 71.84, 71.65, 69.35, 68.08, 62.88, 50.28, 36.66, 35.04, 31.87, 31.20, 30.19, 29.75, 29.67, 29.64, 29.50, 29.48, 29.38, 29.37, 29.31, 29.04, 25.87, 25.64, 22.64, 14.07. HRMS (ESI) calculated for C$_{79}$H$_{108}$NO$_{10}$ [M+H]$^+$: 1230.7973, found: 1230.7968.

Synthesis of 3,4-di-O-benzyl-1-O-(2,3-di-O-benzyl-4,6-O-benzylidene-α-D-galactopyranosyl)-2-(11-(3,4-difluorophenyl)undecanoyl)amino-D-ribo-octadecan-1,3,4-trio 1 (A11)

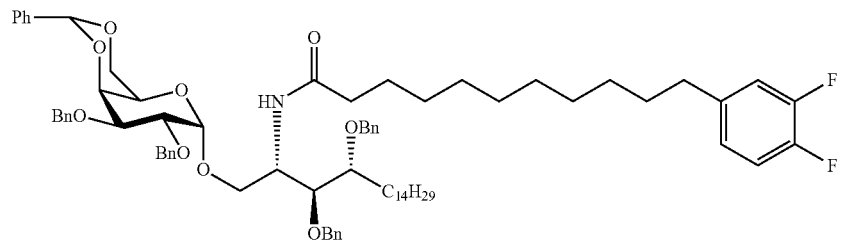

By the similar procedure of synthesis of A8, compound A7 (100 mg, 0.105 mmol) and B14 (28 mg, 0.093 mmole) were used as starting materials to afford A11 (63 mg, 0.052 mmol, 56%). mp: 98° C. $^1$H-NMR (CDCl$_3$, 400 MHz) δ 7.21-7.54 (m, 25H), 6.92-7.06 (m, 2H), 6.81-6.87 (m, 1H), 5.87 (d, J=8.4 Hz, 1H), 5.45 (s, 1H), 4.95 (d, J=3.2, 1H), 4.84 (d, J=11.6 Hz, 1H), 4.69-4.79 (m, 3H), 4.63 (d, J=11.6 Hz, 1H), 4.58 (d, J=11.6 Hz, 1H), 4.50 (d, J=11.6 Hz, 1H), 4.49 (d, J=11.6 Hz, 1H), 4.25-4.33 (m, 1H), 4.17 (d, J=2.8 Hz, 1H) 4.04-4.13 (m, 2H), 3.88-3.97 (m, 3H), 3.74-3.81 (m, 2H), 3.57 (s, 1H), 3.51-3.56 (m, 1H), 2.54 (t, J=7.6 Hz, 2H), 1.82-1.96 (m, 2H), 1.15-1.69 (m, 42H), 0.89 (t, J=6.8 Hz, 3H). $^{13}$C-NMR (CDCl$_3$, 100 MHz) δ 172.84, 150.02 (dd, J=245, 13 Hz), 148.55 (dd, J=244, 13 Hz), 139.68, 138.60, 138.49, 138.46, 138.36, 137.77, 128.81, 128.39, 128.32, 128.28, 128.26, 128.05, 127.86, 127.79, 127.78, 127.66, 127.54, 126.26, 124.00, 116.89, 116.72, 100.96, 99.54, 79.75, 79.46, 76.01, 75.66, 74.29, 73.79, 73.25, 71.84, 71.65, 69.35, 68.08, 62.88, 50.28, 36.66, 35.04, 31.87, 31.20, 30.19, 29.75, 29.67, 29.64, 29.50, 29.48, 29.38, 29.37, 29.31, 29.04, 25.78, 25.64, 22.64, 14.07. HRMS (ESI) calculated for C$_{76}$H$_{100}$F$_2$NO$_9$[M+H]$^+$: 1208.7366, found: 1208.7398.

Synthesis of 3,4-di-O-benzyl-1-O-(2,3-di-O-benzy-4,6-O-benzylidene-α-D-galactopyranosyl)-2-(11-(2,4-difluorophenyl)undecanoyl)amino-D-ribo-octadecan-1,3,4-triol (A12)

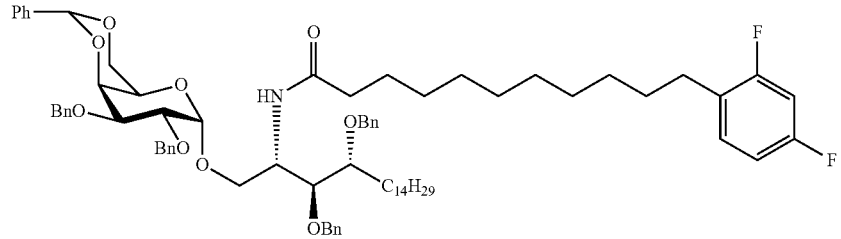

By the similar procedure of synthesis of A8, compound A6 (100 mg, 0.105 mmol) and B15 (28 mg, 0.093 mmole) were used as starting materials to afford A12 (70 mg, 0.058 mmol, 62%) as white wax. $^1$H-NMR (CDCl$_3$, 400 MHz) δ 7.20-7.55 (m, 25H), 7.04-7.14 (m, 1H), 6.69-6.81 (m, 2H), 5.89 (d, J=8.3 Hz, 1H), 5.45 (s, 1H), 4.95 (d, J=3.2 Hz, 1H), 4.85 (d, J=11.6 Hz, 1H), 4.70-4.79 (m, 3H), 4.64 (d, J=11.6 Hz, 1H), 4.58 (d, J=11.6 Hz, 1H), 4.50 (d, J=11.6 Hz, 1H), 4.49 (d, J=11.6 Hz, 1H), 4.25-4.33 (m, 1H), 4.17 (d, J=2.8 Hz, 1H) 4.04-4.13 (m, 2H), 3.88-3.97 (m, 3H), 3.74-3.80 (m, 2H), 3.57 (s, 1H), 3.51-3.56 (m, 1H), 2.57 (t, J=7.6 Hz, 2H), 1.82-1.96 (m, 2H), 1.15-1.69 (m, 42H), 0.88 (t, J=6.6 Hz, 3H). $^{13}$C-NMR (CDCl$_3$, 100 MHz) δ 172.90, 162.30, 138.59, 138.50, 138.45, 138.36, 137.78, 130.89, 128.82, 128.40, 128.33, 128.30, 128.27, 128.06, 127.87, 127.79, 127.68, 127.55, 126.27, 110.07, 103.41, 99.53, 79.75, 79.47, 76.11, 75.67, 74.29, 73.81, 73.27, 71.85, 71.65, 69.36, 68.05, 62.89, 50.29, 36.67, 31.88, 30.19, 30.15, 29.76, 29.67, 29.65, 29.51, 29.37, 29.32, 29.17, 28.38, 25.78, 25.66, 22.65, 14.08. HRMS (ESI) calculated for C$_{76}$H$_{100}$F$_2$NO$_9$ [M+H]$^+$: 1208.7366, found: 1208.7377.

Synthesis of 1-O-(α-D-galactopyranosyl)-2-(11-(4-phenoxyphenyl)undecanoyl)amino-D-ribo-1,3,4-octadecantriol (A15)

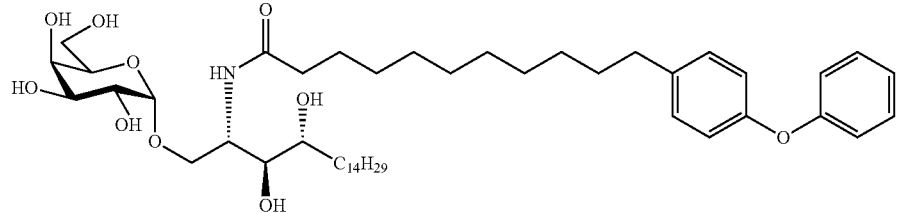

By the procedure similar to C34, A15 (21 mg, 0.026 mmol, 72%) was obtained form A9 (45 mg, 0.036 mmol), as off-white solids. mp: 131° C. $^1$H-NMR (CD$_3$OD/CDCl$_3$=1/1, 400 MHz) δ 7.45 (t, J=8.3 Hz, 2H), 7.28 (d, J=7.7 Hz, 2H), 7.20 (t, J=7.3 Hz, 1H), 7.10 (d, J=8.1 Hz, 2H), 7.04 (d, J=8.1 Hz, 2H), 5.04 (d, J=3.3 Hz, 1H), 4.26 (q, J=7.1 Hz, 1H), 3.79-4.13 (m, 10H), 2.73 (t, J=7.7 Hz, 2H), 2.36 (t, J=7.5 Hz, 2H), 1.65-1.82 (m, 4H), 1.41 (brs, 38H), 0.89 (t, J=7.5 Hz, 3H). $^{13}$C-NMR (CD$_3$OD/CDCl$_3$=1/1, 100 MHz) δ 174.09, 157.18, 154.36, 137.40, 128.98, 128.92, 122.22, 118.25, 117.71, 99.18, 73.88, 71.30, 70.41, 69.68, 69.17, 68.37, 66.63, 61.10, 60.01, 35.80, 34.56, 31.61, 31.29, 31.04, 29.08, 29.02, 28.91, 28.80, 28.72, 28.64, 25.30, 22.01, 19.90, 13.15. [α]$_D^{25}$ +37.4 (c 1.0, CH$_2$Cl$_2$/CH$_3$OH: 1/1). HRMS (ESI) calculated for C$_{47}$H$_{78}$NO$_{10}$ [M+H]$^+$: 816.5626, found: 816.5637.

Synthesis of 1-O-(α-D-Galactopyranosyl)-2-(11-(4-isopropoxy)phenyl)undecanoyl)amino-D-ribo-1,3,4-octadecantriol (A16)

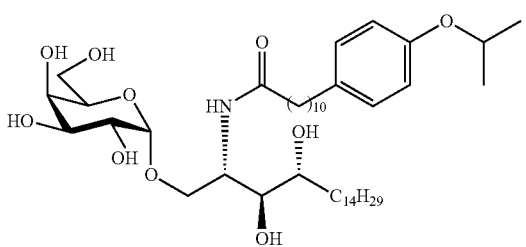

By the procedure similar to C34, compound A16 (34 mg, 0.044 mmol, 74%) was obtained from A10 (72 mg, 0.059 mmol). The data of A16: mp: 120° C. $^1$H-NMR (CD$_3$OD/CDCl$_3$=1/1, 400 MHz) δ 7.16 (d, J=8.5 Hz, 2H), 6.90 (d, J=8.5 Hz, 2H), 5.01 (d, J=3.7 Hz, 1H), 4.58-4.66 (m, 1H), 4.32 (m, 1H), 4.03 (d, J=2.6 Hz, 1H), 3.99 (dd, J=10.6, 4.8, 1H), 3.88-3.96 (m, 2H), 3.78-3.88 (m, 4H), 3.62-3.73 (m, 2H), 2.64 (t, J=7.6 Hz, 2H), 2.32 (t, J=7.4 Hz, 2H), 1.61-1.81 (m, 4H), 1.32-1.52 (m, 44H), 0.99 (t, J=6.8 Hz, 3H). $^{13}$C-NMR (CD$_3$OD/CDCl$_3$=1/1, 100 MHz) δ 174.06, 155.10, 134.52, 128.54, 115.33, 99.16, 73.81, 71.25, 70.40, 69.65, 69.62, 69.12, 68.33, 66.60, 61.04, 35.75, 35.70, 34.35, 31.53, 31.25, 31.08, 29.09, 29.03, 28.97, 28.94, 28.87, 28.85, 28.76, 28.68, 28.59, 25.27, 25.22, 21.96, 21.08, 20.88, 13.08. [α]$_D^{25}$ +36.2 (c 1.0, CH$_2$Cl$_2$/CH$_3$OH: 1/1). HRMS (ESI) calculated for C$_{44}$H$_{79}$NO$_{10}$Na [M+Na]$^+$: 804.5602, found: 804.5641.

Synthesis of 1-O-(α-D-galactopyranosyl)-2-(11-(3,4-difluorophenyl)undecanoyl)amino-D-ribo-1,3,4-octadecantriol (A17)

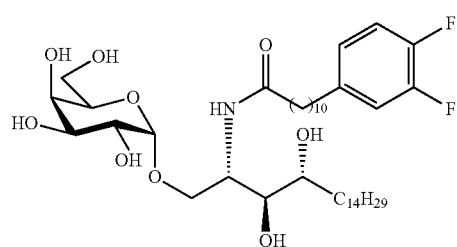

By the procedure similar to C34, compound A17 (37 mg, 0.049 mmol, 94%) was obtained from A11 (63 mg, 0.052 mmol). The data of A18: mp: 140° C. $^1$H-NMR (CD$_3$OD/CDCl$_3$=1/1, 400 MHz) δ 7.06-7.22 (m, 2H), 6.98-7.04 (m, 1H), 5.03 (d, J=3.3 Hz, 1H), 4.29-4.36 (m, 1H), 4.05 (d, J=2.5 Hz, 1H), 4.00 (dd, J=10.5, 4.8, 1H), 3.89-3.96 (m, 2H), 3.78-3.89 (m, 4H), 3.64-3.73 (m, 2H), 2.69 (t, J=7.5 Hz, 2H), 2.34 (t, J=7.6 Hz, 2H), 1.63-1.83 (m, 4H), 1.33-1.48 (m, 38H), 1.00 (t, J=6.5 Hz, 3H). $^{13}$C-NMR (CD$_3$OD/CDCl$_3$=1/1, 100 MHz) δ 174.07, 149.33 (d, J=247, 13 Hz), 147.95 (d, J=244, 13 Hz), 139.47, 123.56, 116.22, 116.06, 99.18, 73.86, 71.82, 70.40, 69.67, 69.15, 68.34, 66.63, 61.08, 45.00, 35.78, 35.73, 34.40, 31.58, 31.28, 30.66, 29.12, 29.06, 29.00, 28.91, 28.85, 28.77, 28.71, 28.44, 25.28, 21.99, 13.12. [α]$_D^{25}$ +44.4 (c 1.0, CH$_2$Cl$_2$/CH$_3$OH: 1/1). HRMS (ESI) calculated for C$_{41}$H$_{72}$F$_2$NO$_9$ [M+H]$^+$: 760.5175, found: 760.5222.

Synthesis of 1-O-(α-D-galactopyranosyl)-2-(11-(2,4-difluorophenyl)undecanoyl)amino-D-ribo-1,3,4-octadecantriol (A18)

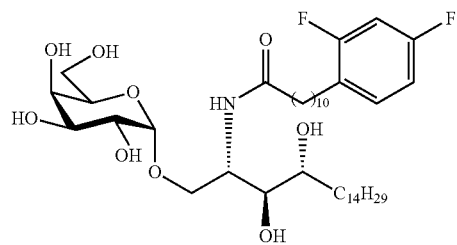

By the procedure similar to C34, compound A18 (39 mg, 0.051 mmol, 88%) was obtained from compound A12 (70 mg, 0.058 mmol). The data of A18: mp: 149° C. $^1$H-NMR (CD$_3$OD/CDCl$_3$=1/1, 400 MHz) δ 7.29 (q, J=8.1 Hz, 1H), 6.87-6.97 (m, 2H), 5.05 (d, J=3.7 Hz, 1H), 4.30-4.38 (m, 1H), 4.07 (d, J=2.9 Hz, 1H), 4.03 (dd, J=10.6, 4.4 Hz, 1H), 3.91-3.98 (m, 2H), 3.66-3.75 (m, 4H), 3.64-3.73 (m, 2H), 2.73 (t, J=7.5 Hz, 2H), 2.36 (t, J=7.6 Hz, 2H), 1.65-1.86 (m, 4H), 1.24-1.60 (m, 38H), 1.02 (t, J=6.6 Hz, 3H). $^{13}$C-NMR (CD$_3$OD/CDCl$_3$=1/1, 100 MHz) δ 174.09, 161.65, 159.20, 130.48, 124.73, 110.06, 102.62, 99.19, 73.90, 71.31, 70.40, 69.69, 69.17, 68.36, 66.66, 61.11, 50.12, 35.81, 35.76, 31.63, 31.30, 29.59, 29.16, 29.14, 29.09, 29.02, 28.92, 28.87, 28.78, 28.76, 28.73, 28.56, 27.72, 25.30, 22.01, 13.16. [α]$_D^{25}$ +46.0 (c 1.0, CH$_2$Cl$_2$/CH$_3$OH: 1/1). HRMS (ESI) calculated for C$_{41}$H$_{71}$F$_2$NO$_9$Na [M+Na]$^+$: 782.4995, found: 782.5034.

Synthesis of 1-O-(α-D-galactopyranosyl)-2-((10R,11S)-11-(3,4-difluorophenyl)-10,11-dihydroxyundecanoyl)amino-D-ribo-1,3,4-octadecantriol and 1-O-(α-D-galactopyranosyl)-2-((10S,11R)-11-(3,4-difluorophenyl)-10,11-dihydroxyundecanoyl)amino-D-ribo-1,3,4-octadecantriol (A19) as a mixture of anti-diol isomers

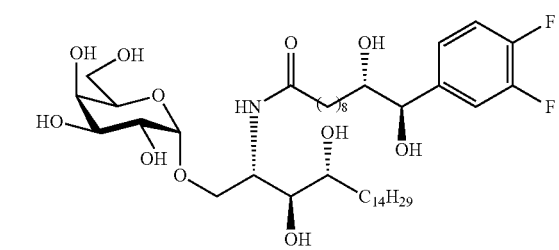

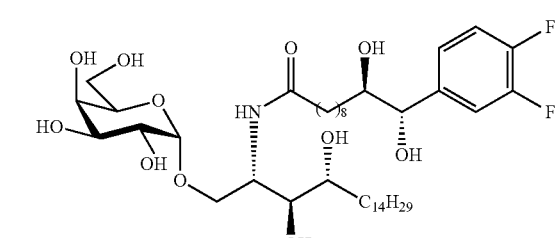

To the solution of A7 (101 mg, 0.109 mmol) in dichloromethane (3 mL) was added anti-B21 (32 mg, 0.097 mmol), HBTU (62 mg, 0.16 mmol) and NMM (24 μL, 0.23 mmol). After stirring at room temperature for 12 h, the mixture was concentrated and the residue was purified by column chromatography (ethyl acetate/n-hexane=1/4 to 1/2 to 1/1). The resulting white wax was dissolved in dichloromethane/methanol (1/1, 10 mL) and Pd(OH)$_2$ (10 mg) was then added. After stirring at room temperature under hydrogen for 15 h, the mixture was filtered through Celite pad and washed with dichloromethane/methanol (1/1). The filtrate was concentrated and the residue was purified by column chromatography (dichloromethane/methanol=10/1 then 8/1) to afford A19 (34 mg, 0.043 mmol, 44%) as off-white solids. mp: 105° C. $^1$H-NMR (CDCl$_3$/CD$_3$OD=1/1, 400 MHz) δ 7.17-7.40 (m, 3H), 5.01 (d, J=3.6 Hz, 1H), 4.62 (d, J=4.8 Hz, 0.75H), 4.50 (d, J=6.0 Hz, 0.25H), 4.28-4.36 (m, 1H), 4.03 (d, J=2.8 Hz, 1H), 3.99 (dd, J=4.8, 10.8 Hz, 1H), 3.87-3.95 (m, 2H), 3.76-3.87 (m, 4H), 3.61-3.71 (m, 2H), 2.31 (t, J=7.4 Hz, 2H), 1.31-1.83 (m, 40H), 0.99 (t, J=6.9 Hz, 3H). $^{13}$C-NMR (CDCl$_3$/CD$_3$OD=1/1, 100 MHz) δ 173.97, 149.42 (dd, J=245, 13 Hz), 148.86 (dd, J=245, 13 Hz), 136.65, 122.46, 116.09, 115.77, 115.27, 115.10, 99.16, 75.70, 75.35, 74.74, 74.21, 73.94, 71.25, 70.40, 69.65, 69.10, 68.31, 66.52, 61.03, 49.91, 35.63, 31.94, 31.69, 31.23, 31.18, 29.09, 29.04, 29.00, 28.95, 28.83, 28.76, 28.68, 28.65, 28.53, 25.17, 25.08, 24.96, 21.94, 13.04. $[\alpha]_D^{25}$ +58.3 (c 1.0, $CH_2Cl_2/CH_3OH$: 1/1). HRMS (ESI) calculated for $C_{41}H_{71}F_2NO_{11}Na$ $[M+Na]^+$: 814.4893, found: 814.4859.

Synthesis of 1-O-(α-D-galactopyranosyl)-2-((10S, 11S)-11-(3,4-difluorophenyl)-10,11-dihydroxyundecanoyl)amino-D-ribo-1,3,4-octadecantriol and 1-O-(α-D-galactopyranosyl)-2-((10R,11R)-11-(3,4-difluorophenyl)-10,11-dihydroxyundecanoyl)amino-D-ribo-1,3,4-octadecantriol, (A20) as a mixture of syn-diol isomers

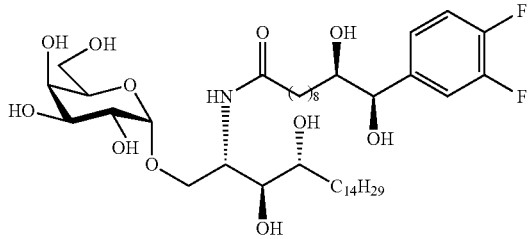

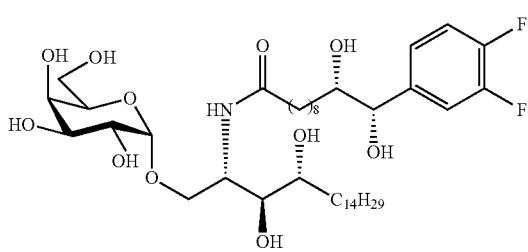

To the solution of A7 (101 mg, 0.109 mmol) in dichloromethane (3 mL) was added Syn-A21 (14 mg, 0.042 mmol), HBTU (62 mg, 0.16 mmol) and NMM (24 μL, 0.22 mmol). After stirring at room temperature for 12 h, the mixture was concentrated and the residue was purified by column chromatography (ethyl acetate/n-hexane=1/4 to 1/2 to 1/1). The resulting white wax was dissolved in dichloromethane/methanol (1/1, 10 mL) and Pd(OH)$_2$ (10 mg) was then added. After stirring at room temperature under hydrogen for 15 h, the mixture was filtered through Celite pad and washed with dichloromethane/methanol (1/1). The filtrate was concentrated and the residue was purified by column chromatography (dichloromethane/methanol=10/1 then 8/1) to afford A20 (20 mg, 0.025 mmol, 60%) as white solids. mp: 80° C. $^1$H-NMR (CDCl$_3$/CD$_3$OD=1/1, 400 MHz) δ 7.19-7.49 (m, 3H), 5.02 (d, J=3.6 Hz, 1H), 4.52 (d, J=6 Hz, 1H), 4.30-4.37 (m, 1H), 4.04 (d, J=2.8 Hz, 1H), 4.01 (dd, J=4.4, 10.8 Hz, 1H), 3.89-3.96 (m, 2H), 3.78-3.88 (m, 4H), 3.63-3.73 (m, 3H), 2.33 (t, J=7.6 Hz, 2H), 1.26-1.84 (m, 40H), 1.01 (t, J=6.8 Hz, 3H). $^{13}$C-NMR (CDCl$_3$/CD$_3$OD=1/1, 100 MHz) δ 174.00, 149.58 (dd, J=245, 12 Hz), 149.07 (dd, J=245, 12 Hz), 138.90, 122.46, 116.13, 115.14, 99.21, 75.47, 74.79, 74.01, 71.28, 70.41, 69.69, 69.15, 68.34, 66.57, 61.09, 49.90, 35.67, 31.98, 31.77, 31.27, 29.12, 29.03, 28.98, 28.80, 28.68, 28.56, 25.20, 25.00, 21.98, 13.08. $[\alpha]_D^{25}$ +50.0 (c 1.0, $CH_2Cl_2$/$CH_3OH$: 1/1). HRMS (ESI) calculated for $C_{41}H_{71}F_2NO_{11}Na$ $[M+Na]^+$: 814.4893, found: 814.4893.

Synthesis of 1-O-(α-D-galactopyranosyl)-2-(11-(4-bromophenyl)-10,11-dihydroxyundecanoyl)amino-D-ribo-1,3,4-octadecantriol (A21)

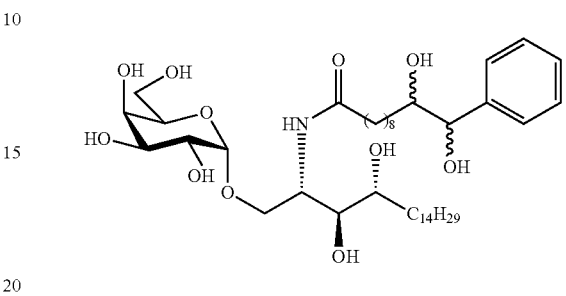

By the procedure similar to A19, compound A21 (18 mg, 0.024 mmol, 28%) was obtained from A7 (90 mg, 0.094 mmol) and B19 (32 mg, 0.086 mmol). The data of A21: off-white wax. $^1$H-NMR (CD$_3$OD/CDCl$_3$=1/1, 400 MHz) δ 7.26-7.51 (m, 5H), 5.02-5.10 (m, 1H), 5.02 (d, J=4.0 Hz, 1H), 4.23-4.29 (m, 1H), 4.06-4.15 (m, 1H), 3.97-4.03 (m, 2H), 3.83-3.96 (m, 6H), 3.68 (t, J=10.2 Hz, 1H), 2.84-2.89 (m, 1H), 2.52 (t, J=7.4 Hz, 2H), 1.27-1.89 (m, 40H), 1.02 (t, J=6.8 Hz, 3H). $^{13}$C-NMR (CD$_3$OD/CDCl$_3$=1/1, 150 MHz) δ 174.08, 173.54, 138.50, 128.72, 127.55, 125.39, 99.10, 72.40, 71.92, 70.84, 70.16, 69.92, 69.57, 69.24, 68.23, 63.43, 61.13, 52.30, 43.34, 36.69, 36.39, 35.91, 35.69, 35.26, 33.69, 32.83, 32.03, 31.67, 31.25, 30.90, 30.59, 29.81, 29.30, 29.01, 28.97, 28.86, 28.77, 28.67, 28.54, 28.46, 25.22, 25.00, 24.36, 24.27, 21.97, 13.09. $[\alpha]_D^{25}$ +22.7 (c 1.0, $CH_2Cl_2$/$CH_3OH$: 1/1). HRMS (ESI) calculated for $C_{41}H_{74}NO_{11}$ $[M+H]^+$: 778.5081, found: 778.5073.

Scheme 2: Synthesis of Compound A23-25

Synthesis of 1-O-(α-D-galactopyranosyl)-2-amino-D-ribo-1,3,4-octadecantriol (A22)

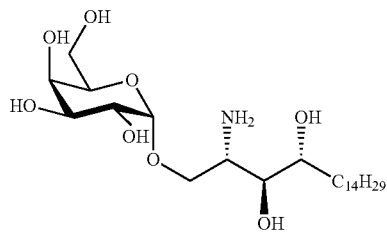

To the solution of A7 (520 mg, 0.545 mmol) in dichloromethane/methanol (1/1, 20 mL) was added Pd(OH)$_2$ (220 mg) and three drops of acetic acid. The reaction mixture was stirred at room temperature under 80 psi hydrogen for 16 h. The mixture was filtered through Celite and the filter cake was washed with methanol. The filtrate was concentrated and dried in vacuum to afford crude A22 (302 mg, quantitative) as white solids. HRMS (ESI) calculated for $C_{24}H_{49}NO_8H$ [M+H]$^+$: 480.3536, found: 480.3515.

Synthesis of 1-O-(α-D-galactopyranosyl)-2-(11-(3,4-dichlorophenyl)undecanoyl)amino-D-ribo-1,3,4-octadecantriol (A23)

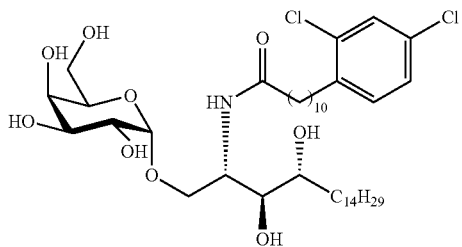

To the solution of A22 (50 mg, 0.10 mmol) in dichloromethane/methanol (1/1, 3 mL) was added B16 (34 mg, 0.10 mmol), HBTU (59 mg, 0.16 mmol) and NMM (23 μL, 0.21 mmol). The reaction mixture was stirred at room temperature for 12 h. The mixture was concentrated and the residue was purified by column chromatography (dichloromethane/methanol=15/1 to 12/1 to 9/1) to afford A23 (16 mg, 0.020 mmol, 20%) as off-white solids. mp: 147° C. $^1$H-NMR (CD$_3$OD/CDCl$_3$=1/1, 400 MHz) δ 7.51 (s, 1H), 7.35 (s, 2H), 5.08 (d, J=3.3 Hz, 1H), 4.33-4.43 (m, 1H), 4.08-4.12 (m, 1H), 4.06 (dd, J=10.7, 4.0 Hz, 1H), 3.82-4.02 (m, 6H), 3.67-3.77 (m, 2H), 2.86 (t, J=7.6 Hz, 2H), 2.39 (t, J=7.5 Hz, 2H), 1.66-1.88 (m, 4H), 1.34-1.60 (m, 38H), 1.06 (t, J=6.4 Hz, 3H). $^{13}$C-NMR (CD$_3$OD/CDCl$_3$=1/1, 100 MHz) δ 174.05, 138.47, 133.89, 131.36, 130.64, 128.41, 126.35, 99.25, 73.99, 71.36, 70.42, 69.74, 69.22, 68.42, 66.71, 61.19, 49.97, 35.82, 32.41, 31.76, 31.34, 29.20, 29.17, 29.12, 29.06, 28.95, 28.91, 28.81, 28.76, 28.69, 25.33, 25.29, 22.06, 13.21. [α]$_D^{25}$ +46.8 (c 1.0, CH$_2$Cl$_2$/CH$_3$OH: 1/1). HRMS (ESI) calculated for $C_{41}H_{71}Cl_2NO_9Na$ [M+Na]$^+$: 814.4404, found: 814.4311

Synthesis of 1-O-(α-D-galactopyranosyl)-2-(11-(4-chlorophenyl)undecanoyl)amino-D-ribo-1,3,4-octadecantriol (A24)

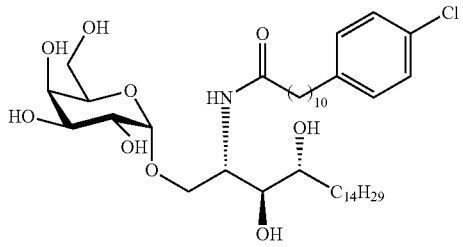

By the procedure similar to A23, compound A24 (18 mg, 0.024 mmol, 22%) was obtained from A22 (52 mg, 0.11 mmol) and B17 (32 mg, 0.11 mmol). The data of A24: off-white solids. mp: 136° C. $^1$H-NMR (CD$_3$OD/CDCl$_3$=1/1, 400 MHz) δ 7.28 (d, J=8.4 Hz, 2H), 7.17 (d, J=8.4 Hz, 2H), 4.96 (d, J=3.6 Hz, 1H), 4.21-4.29 (m, 1H), 3.98 (d, J=2.5 Hz, 1H), 3.95 (dd, J=10.6, 4.4, 1H), 3.83-3.90 (m, 2H), 3.72-3.82 (m, 4H), 3.58-3.68 (m, 2H), 2.64 (t, J=7.6 Hz, 2H), 2.28 (t, J=7.8 Hz, 2H), 1.57-1.77 (m, 4H), 1.20-1.51 (m, 38H), 0.95 (t, J=6.7 Hz, 3H). $^{13}$C-NMR (CD$_3$OD/CDCl$_3$=1/1, 100 MHz) δ 173.99, 140.73, 130.53, 129.08, 127.51, 99.15, 73.79, 71.23, 70.34, 69.62, 69.17, 68.32, 66.58, 61.06, 49.87, 35.67, 34.52, 31.53, 31.23, 30.73, 29.01, 28.95, 28.87, 28.81, 28.75, 28.65, 28.46, 25.24, 21.94, 13.03. [α]$_D^{25}$ +41.7 (c 1.0, CH$_2$Cl$_2$/CH$_3$OH: 1/1). HRMS (ESI) calculated for $C_{41}H_{72}ClNO_9Na$ [M+Na]$^+$: 780.4793, found: 780.4779.

Synthesis of 1-O-(α-D-galactopyranosyl)-2-(11-(4-bromophenyl)undecanoyl)amino-D-ribo-1,3,4-octadecantriol (A25)

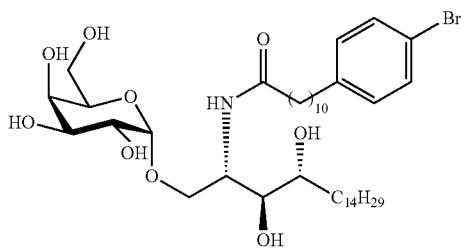

By the procedure similar to A23, compound A25 (22 mg, 0.027 mmol, 25%) was obtained from A22 (52 mg, 0.11 mmol) and B28 (56 mg, 0.16 mmol). The data of A25: off-white wax. $^1$H-NMR (CD$_3$OD/CDCl$_3$=1/1, 400 MHz) δ 7.28 (d, J=8.4 Hz, 2H), 7.20-7.47 (m, 2H), 5.00 (d, J=3.6 Hz, 1H), 4.28-4.33 (m, 1H), 4.02 (d, J=2.8 Hz, 1H), 3.98 (dd, J=10.6, 4.6 Hz, 1H), 3.863-3.94 (m, 2H), 3.77-3.87 (m, 4H), 3.62-3.70 (m, 2H), 2.69 (t, J=7.6 Hz, 2H), 2.31 (t, J=7.6 Hz, 2H), 1.29-1.81 (m, 42H), 0.98 (t, J=6.6 Hz, 3H). $^{13}$C-NMR (CD$_3$OD/CDCl$_3$=1/1, 100 MHz) δ 171.21, 141.18, 130.44, 129.44, 118.39, 99.41, 74.54, 70.41, 70.13, 69.58, 69.50, 69.07, 68.41, 67.22, 60.95, 49.68, 35.58, 34.51, 31.36, 31.18, 30.62, 28.95, 28.90, 28.81, 28.76, 28.68, 28.61, 28.40, 27.00, 25.21, 24.88, 21.89, 19.90, 19.74, 19.57, 12.96. [α]$_D^{25}$ +40.7 (c 1.0, CH$_2$Cl$_2$/CH$_3$OH: 1/1). HRMS (ESI) calculated for $C_{41}H_{73}BrNO_9$ [M+H]$^+$: 802.4469, found: 802.4216.

(3) Synthetic Scheme 3: Synthesis of Aryl-Alkanoic Acid

Synthesis of (9-carboxynonyl)triphenylphosphonium bromide (B2)

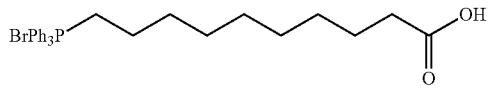

10-Bromodecanoic acid (19.65 g, 78.24 mmol) and triphenylphosphine (21.45 g, 81.78 mmol) were mixed and stirred at 150° C. for 24 h. Wittig reagent B2 as light yellow syrup was obtained in 100% yield and used without further purification.

Synthesis of 11-(4-(4-fluorophenoxy)phenyl))undecanoic acid (B4)

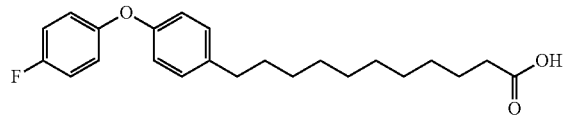 [SMILES: O=C(O)CCCCCCCCCCc1ccc(Oc2ccc(F)cc2)cc1]

To the mixture of B2 (19.89 g, 38.81 mmol) and THF (150 mL) was added potassium t-butoxide (10.40 g, 92.68 mmol) at 0° C. The reaction mixture became a red solution. The reaction mixture was warmed to rt and stirred for 1 h. 4-(4-fluorophenoxy)benzaldehyde (B1) (7.50 g, 34.7 mmol) was added to the reaction mixture at 0° C. and was stirred for an additional 30 min at rt. The reaction mixture was neutralized with 1.0 N HCl and concentrated. The residue was partitioned with ethyl acetate (200 mL), water (200 mL) (pH value was adjusted to 5 by adding 1.0 N HCl) and brine (200 mL). The organic phase was isolated and concentrated under reduced pressure. The residue was recrystallized with ethanol/water (1/1, 80 mL) and washed with water to afford B3 (9.99 g, 27.0 mmol, 78%) as white solids. B3 was dissolved in ethanol/ethyl acetate (1/1, 80 mL) and Pd/C (10%, 1.08 g) was added after then. The mixture was stirred at room temperature under hydrogen for 12 h. The reaction mixture was filtered through Celite pad and washed with ethyl acetate. The filtrate was concentrated and recrystallized with methanol/water (5/1, 12 mL), filtered and washed with water to afford 11-(4-(4-fluorophenoxy)phenyl))undecanoic acid (B4) (9.080 g, 24.38 mmol, 90%) as white solids. mp: 73° C. $^1$H-NMR (CDCl$_3$, 400 MHz) δ 6.85-7.13 (m, 8H), 2.56 (t, J=7.6 Hz, 2H), 2.33 (t, J=7.4 Hz, 2H), 1.22-1.65 (m, 16H). $^{13}$C-NMR (CDCl$_3$, 100 MHz) δ 179.69, 159.78, 157.38, 155.36, 153.39, 137.88, 129.56, 120.09, 120.01, 118.33, 116.25, 116.02, 35.18, 33.97, 31.59, 29.69, 29.48, 29.44, 29.38, 29.24, 29.20, 29.03, 24.65. HRMS (ESI) calculated for C$_{23}$H$_{29}$FO$_3$Na [M+Na]$^+$: 395.1998, found: 395.2003.

Synthesis of 11-(4-phenoxy)phenylundecanoic acid (B12)

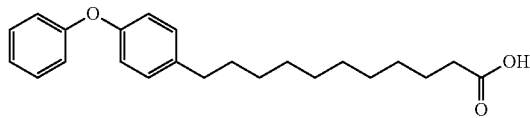 [SMILES: O=C(O)CCCCCCCCCCc1ccc(Oc2ccccc2)cc1]

Similar to the route for compound B4, compound B12 (1.34 g, 3.78 mmol, 97%) was synthesized from B2 (3.47 g, 6.76 mmol) and 4-phenoxybenzaldehyde (1.03 g, 5.20 mmol). Data for compound B12: off-white solids, mp: 55° C. $^1$H-NMR (CDCl$_3$, 400 MHz) δ 6.93-7.35 (m, 9H), 2.60 (t, J=7.4 Hz, 2H), 2.37 (t, J=7.3 Hz, 2H), 1.65 (m, 4H), 1.33 (m, 12H). $^{13}$C-NMR (CDCl$_3$, 100 MHz) δ 180.35, 157.71, 154.83, 137.87, 130.13, 129.51, 122.73, 118.97, 118.32, 35.18, 34.10, 31.55, 29.45, 29.42, 29.36, 29.22, 29.18, 29.00, 24.63. HRMS (ESI) calculated for C$_{23}$H$_{30}$O$_3$Na [M+Na]$^+$: 377.2093, found: 377.2053.

Synthesis of 11-(4-isopropoxy)phenylundecanoic acid (B13)

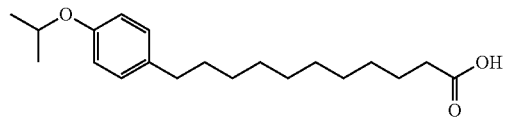 [SMILES: CC(C)Oc1ccc(CCCCCCCCCCC(=O)O)cc1]

By the similar procedure of synthesis of B4, compound B2 (2.25 g, 4.38 mmol) and 4-isopropoxybenzaldehyde (479 mg, 2.92 mmole) were used as starting materials to afford compound B13 (562 mg, 1.75 mmol, 60%) as white solids. mp: 46° C. $^1$H-NMR (CDCl$_3$, 400 MHz) 7.04 (d, J=8.5 Hz, 2H), 6.78 (d, J=8.6 Hz, 2H), 4.48 (m, 1H), 2.50 (t, J=7.5 Hz, 2H), 2.32 (t, J=7.5 Hz, 2H), 1.50-1.61 (m, 4H), 1.25-1.35 (m, 18H). $^{13}$C-NMR (CDCl$_3$, 100 MHz) 179.73, 155.82, 134.93, 129.20, 115.77, 69.91, 35.04, 34.11, 31.69, 29.50, 29.47, 29.40, 29.26, 29.22, 29.12, 29.06, 24.71, 22.11, 21.88. HRMS (ESI) calculated for C$_{20}$H$_{32}$O$_3$Na [M+Na]$^+$: 343.2249, found: 343.2227.

Synthesis of (10 E or 10Z))-11-(3,4-difluorophenyl) undec-10-enoic acid ((E)-B7, and (Z)-B7)

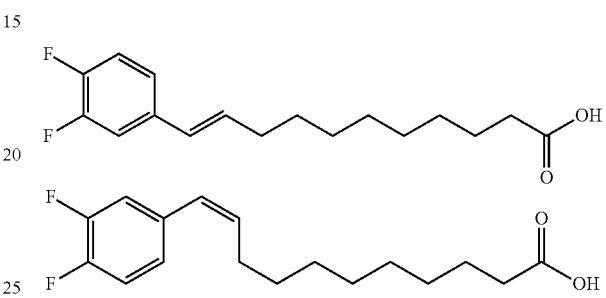

By the similar procedure to compound B3, B2 (12.93 g, 25.18 mmol) and THF (80 mL) and 3,4-difluorobenzaldehyde (2.35 g, 16.5 mmol) were starting materials to give compound B7 (3.77 g, 12.7 mmol, 77%). The Z-form and E-form products were separated by recrystallization with n-hexane. (E)-B7 was obtained as white solids. mp: 66° C. $^1$H-NMR (CDCl$_3$, 400 MHz) 6.98-7.14 (m, 3H), 6.25 (d, J=15.8 Hz, 1H), 6.12 (m, 1H), 2.33 (t, J=7.5 Hz, 2H), 2.16 (q, J=7.0 Hz, 2H), 1.61 (m, 2H), 1.43 (m, 2H), 1.30 (s, 8H). $^{13}$C-NMR (CDCl$_3$, 100 MHz) 180.57, 150.49 (dd, J=246, 12 Hz), 149.31 (dd, J=241, 13 Hz), 135.29, 132.35, 127.88, 121.99, 117.13, 114.18, 34.15, 32.91, 29.31, 29.22, 29.18, 29.08, 24.70. HRMS (ESI) calculated for C$_{17}$H$_{22}$F$_2$O$_2$Na [M+Na]$^+$: 319.1486, found: 319.1485. (Z)-B7 was obtained as colorless oil with 25% inseparable (E)-B7.

Synthesis of (3,4-difluorophenyl)undecanoic acid (B14)

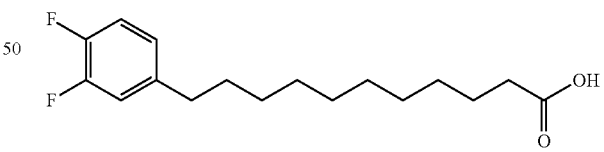

Compound B7 (1.61 g, 5.43 mmol) was dissolved in ethanol/ethyl acetate (1/1, 30 mL) and Pd/C (10%, 160 mg) was added to the solution. The mixture stirred at room temperature under hydrogen for 12 h. The mixture was filtered through Celite pad and washed with ethyl acetate. The filtrate was concentrated and dried in vacuum. Compound B14 was obtained as white solids (1.61 g, 5.40 mmol, 99%). mp: 51° C. $^1$H-NMR (CDCl$_3$, 400 MHz) δ 6.90-7.03 (m, 2H), 6.84 (m, 1H), 2.53 (t, J=7.7 Hz, 2H), 2.33 (t, J=7.5 Hz, 2H), 1.52-1.64 (m, 4H), 1.26 (m, 12H). $^{13}$C-NMR (CDCl$_3$, 100 MHz) δ 180.24, 150.13 (dd, J=13, 247 Hz), 148.49 (dd, J=13, 246 Hz), 147.40, 139.77, 124.05, 116.85, 35.09, 34.01, 31.23, 29.43, 29.36, 29.35, 29.18, 29.05, 29.01, 24.64. HRMS (ESI) calculated for $C_{17}H_{24}F_2O_2Na$ $[M+Na]^+$: 321.1642, found: 321.1594.

Synthesis of 11-(2,4-difluorophenyl)undecanoic acid (B15)

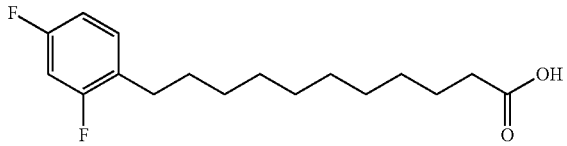 [SMILES: O=C(O)CCCCCCCCCCc1ccc(F)cc1F]

By the similar procedure of synthesis of B4, compound B2 (2.76 g, 5.38 mmol) and 2,4-difluorobenzaldehyde (588 mg, 4.14 mmole) were used as starting materials to afford compound B15 (431 mg, 1.45 mmol, 35%) as off-white solids. mp: 56° C. $^1$H-NMR (CDCl$_3$, 400 MHz) δ 7.05-7.13 (m, 1H), 6.70-6.79 (m, 2H), 2.66 (t, J=7.6 Hz, 2H), 2.31 (t, J=7.4 Hz, 2H), 1.50-1.62 (m, 4H), 1.26 (m, 12H). $^{13}$C-NMR (CDCl$_3$, 100 MHz) δ 180.00, 162.19, 159.80, 130.90, 125.31, 110.69, 103.44, 34.11, 30.15, 29.44, 29.36, 29.33, 29.19, 29.16, 29.03, 28.41, 24.69. HRMS (ESI) calculated for $C_{17}H_{24}F_2O_2Na$ $[M+Na]^+$: 321.1642, found: 321.1637.

Synthesis of 11-(2,4-dichlorophenyl)undecanoic acid (B16)

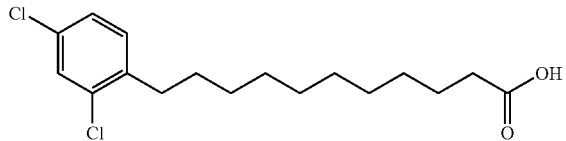 [SMILES: O=C(O)CCCCCCCCCCc1ccc(Cl)cc1Cl]

By the similar procedure of compound B7, B2 (2.25 g, 4.38 mmol) and 2,4-dichlorobenzaldehyde (500 mg, 2.86 mmol) were used as starting materials to afford (10 E or 10Z))-11-(2,4-dichlorophenyl)undec-10-enoic acid (B9) (576 mg, 1.75 mmol, 61%). Then this compound (210 mg, 0.638 mmol) was dissolved in ethyl acetate (10 mL) and Pd/BaSO$_4$ (21 mg) was then added. The mixture was stirred at room temperature under hydrogen for 12 h. The mixture was filtered through Celite pad and washed with ethyl acetate. The combined filtrate was concentrated and dried in vacuum to afford compound B16 (210 mg, 0.634 mmol, 99%) as white solids. mp: 78° C. $^1$H-NMR (CDCl$_3$, 400 MHz) δ 7.32 (d, J=1.9 Hz, 1H), 7.09-7.15 (m, 2H), 2.65 (t, J=7.8 Hz, 2H), 2.33 (t, J=7.5 Hz, 2H), 1.53-1.63 (m, 4H), 1.26 (m, 12H). $^{13}$C-NMR (CDCl$_3$, 100 MHz) δ 180.00, 162.19, 159.80, 130.90, 125.31, 110.69, 103.44, 34.11, 30.15, 29.44, 29.36, 29.33, 29.19, 29.16, 29.03, 28.41, 24.69. HRMS (ESI) calculated for $C_{17}H_{24}Cl_2O_2Na$ $[M+Na]^+$: 353.1051, found: 353.1046.

Synthesis of 11-(4-Chlorophenyl)undecanoic acid (B17)

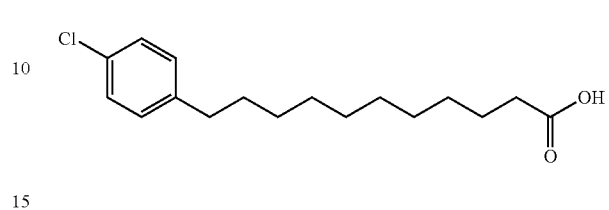

By the similar procedure of synthesis of B10, compound B2 (2.20 g, 4.28 mmol) and 4-chlorobenzaldehyde (401 mg, 2.85 mmole) were used as starting materials to afford B17 (526 mg, 1.77 mmol, 62%). mp: 93° C. $^1$H-NMR (CDCl$_3$, 400 MHz) δ 7.21 (d, J=8.4 Hz, 1H), 7.08 (d, J=8.4 Hz, 2H), 2.54 (t, J=7.5 Hz, 2H), 2.33 (t, J=7.5 Hz, 2H), 1.53-1.63 (m, 4H), 1.26 (m, 12H). $^{13}$C-NMR (CDCl$_3$, 100 MHz) δ 179.90, 141.28, 131.21, 129.71, 128.27, 35.26, 34.00, 31.35, 29.69, 29.44, 29.39, 29.36, 29.19, 29.13, 29.01, 24.64. HRMS (ESI) calculated for $C_{17}H_{25}ClO_2Na$ $[M+Na]^+$: 319.1441, found: 319.1435.

Synthesis of 11-(4-bromophenyl)undecanoic acid (B18)

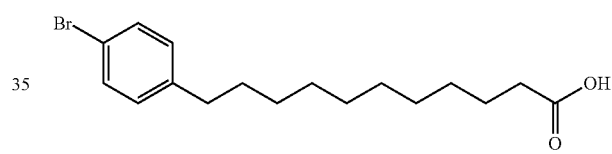

By the similar procedure of synthesis of B10, compound B2 (330 mg, 0.643 mmol) and 4-bromobenzaldehyde (91.5 mg, 0.495 mmole) were used as starting materials to afford B18 (98.0 mg, 0.287 mmol, 58%) as off-white solids. mp: 91° C. $^1$H-NMR (CDCl$_3$, 400 MHz) δ 7.37 (d, J=8.3 Hz, 1H), 7.02 (d, J=8.3 Hz, 2H), 2.53 (t, J=7.6 Hz, 2H), 2.34 (t, J=7.5 Hz, 2H), 1.52-1.63 (m, 4H), 1.20-1.37 (m, 12H). $^{13}$C-NMR (CDCl$_3$, 100 MHz) δ 179.94, 141.79, 141.79, 131.22, 130.14, 119.22, 35.31, 34.11, 31.27, 29.44, 29.38, 29.36, 29.19, 29.12, 29.03, 24.68. HRMS (ESI) calculated $C_{17}H_{26}BrO_2$ $[M+H]^+$: 341.1116, found: 341.1111.

11-(4-bromophenyl)-10,11-dihydroxyundecanoic acid (B20)

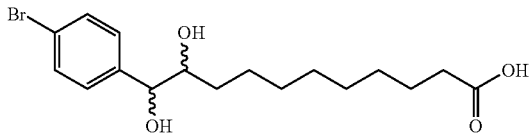 [SMILES: O=C(O)CCCCCCCCC(O)C(O)c1ccc(Br)cc1]

To the solution of B11 (389 mg, 1.15 mmol) in t-butanol/water (4/3, 35 mL) was added NMO (462 mg, 3.94 mmol) and osmium tetroxide (2.5 wt % in t-BuOH, 170 μL, 0.167 mmol). After stirred at room temperature for 15 h, the reaction was quenched with sat. Na$_2$S$_2$O$_3$ and concentrated. The residue was partitioned with dichloromethane (50 mL) and sat. Na$_2$S$_2$O$_3$ (50 mL). The organic phase was washed with brine (50 mL), concentrated and purified by column chromatography (ethyl acetate/n-hexane=1/2 then 1/1) to afford B20 (256 mg, 0.686 mmol, 60%). $^1$H-NMR (CD$_3$OD/CDCl$_3$=1/1, 400 MHz) δ 7.49-7.56 (m, 2H), 7.28-7.37 (m, 2H), 4.59 (d, J=5.1 Hz, 0.7H), 4.44 (d, J=6.6 Hz, 0.3H), 3.71-3.77 (m, 0.7H), 3.62-3.66 (m, 0.3H), 2.45 (t, J=7.2 Hz, 2H), 1.27-1.78 (m, 14H). $^{13}$C-NMR (CD$_3$OD/CDCl$_3$=1/1, 100 MHz) δ 169.05, 140.40, 140.16, 130.60, 130.30, 128.18, 120.64, 120.27, 76.44, 75.80, 74.81, 74.27, 31.88, 30.94, 28.92, 28.78, 28.67, 28.63, 28.56, 28.48, 28.45, 28.38, 25.10, 24.88, 24.28. HRMS (ESI) calculated for C$_{17}$H$_{25}$BrO$_4$Na [M+Na]$^+$: 395.0834, found: 395.0813.

Synthesis of L-(−)-Menthyl (10E)-11-(3,4-difluorophenyl)-undec-10-enoate (Menthyl (E)-B7)

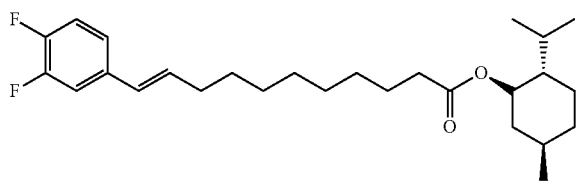

To the solution of (E)-B7 (298 mg, 1.01 mmol) in dichloromethane (3 mL) was added L-(−)-menthol (314 mg, 2.01 mmol), EDC.HCl (347 mg, 1.81 mmol) and DMAP (1.2 mg, 0.010 mmol). The reaction mixture was stirred at room temperature for 12 h. The mixture was diluted with dichloromethane (20 mL), washed with water (20 mL) and concentrated. The residue was purified by column chromatography (ethyl acetate/n-hexane=1/50) to afford Menthyl (E)-B7 (112 mg, 0.258 mmol, 26%) as colorless oil. $^1$H-NMR (CDCl$_3$, 400 MHz) δ 6.95-7.13 (m, 3H), 6.24 (d, J=15.6 Hz, 1H), 6.15-6.24 (m, 1H), 4.11-4.20 (m, 1H), 2.27 (t, J=7.6 Hz, 2H), 2.15 (q, J=6.8 Hz, 2H), 1.92-1.99 (m, 1H), 1.80-1.89 (m, 1H), 1.55-1.68 (m, 4H), 1.38-1.50 (m, 3H), 1.22-1.35 (m, 10H), 0.77-1.09 (m, 9H), 0.73 (d, J=7.0 Hz, 3H). $^{13}$C-NMR (CDCl$_3$, 100 MHz) δ 173.34, 150.39 (dd, J=245, 13 Hz), 149.23 (dd, J=246, 13 Hz), 135.15, 132.24, 127.77, 121.87, 117.00, 114.08, 73.82, 47.00, 40.93, 34.67, 34.25, 32.82, 31.33, 29.67, 29.26, 29.14, 29.08, 29.06, 26.22, 25.06, 23.39, 21.97, 20.70, 16.25. HRMS (ESI) calculated for C$_{27}$H$_{40}$F$_2$O$_2$Na [M+Na]$^+$: 457.2894, found: 457.2863.

Synthesis of (10S,11S)-11-(3,4-difluorophenyl)-10,11-dihydroxyundecanoic acid and (10R,11R)-11-(3,4-difluorophenyl)-10,11-dihydroxyundecanoic acid, syn-(B21) as a mixture of syn-diol isomers

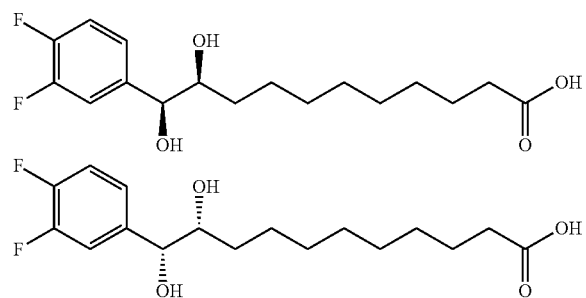

To the solution of menthyl (E)-B7 (110 mg, 0.253 mmol) in t-butanol/water (2/1, 6 mL) was added NMO (103 mg, 0.879 mmol) and osmium tetroxide (2.5 wt % in t-BuOH, 38 μL, 0.0037 mmol). After stirring at room temperature for 20 h, the reaction mixture was quenched with sat. Na$_2$S$_2$O$_3$ (10 mL). The mixture was concentrated and the residue was dissolved in ethyl acetate (20 mL), washed with sat. Na$_2$S$_2$O$_3$ (20 mL), and brine (20 mL), dried over MgSO$_4$, filtered and concentrated. The residue was purified by column chromatography (ethyl acetate/n-hexane=1/4 then 1/3). The resulting colorless oil was dissolved in methanol (5 mL) and 1.0 N NaOH (5 mL) was then added. After stirring at room temperature for 12 h, the reaction mixture was neutralized with 1.0 N HCl (5 mL) and concentrated. The residue was purified by column chromatography (ethyl acetate/n-hexane=1/2 then 1/1) to afford syn-B21 (35 mg, 0.11 mmol, 43%) as white solids. mp: 104° C. $^1$H-NMR (CD$_3$OD, 400 MHz) δ 6.99-7.25 (m, 3H), 4.36 (d, J=5.6 Hz, 1H), 3.45-3.52 (m, 1H), 2.18 (t, J=7.4 Hz, 2H), 1.11-1.54 (m, 14H). $^{13}$C-NMR (CD$_3$OD, 100 MHz) δ 177.70, 151.29 (dd, J=244, 12 Hz), 150.76 (dd, J=244, 13 Hz), 141.48, 124.36, 117.64, 116.87, 77.23, 76.39, 34.39, 33.72, 30.51, 30.41, 30.27, 30.15, 26.80, 26.03. HRMS (ESI) calculated for C$_{17}$H$_{24}$F$_2$O$_4$Na [M+Na]$^+$: 353.1540, found: 353.1550.

Synthesis of (10R,11S)- and (10S,11R)-11-(3,4-difluorophenyl)-(10,11)-dihydroxyundecanoic acid, Anti-(B21) as a mixture of anti-diol isomers

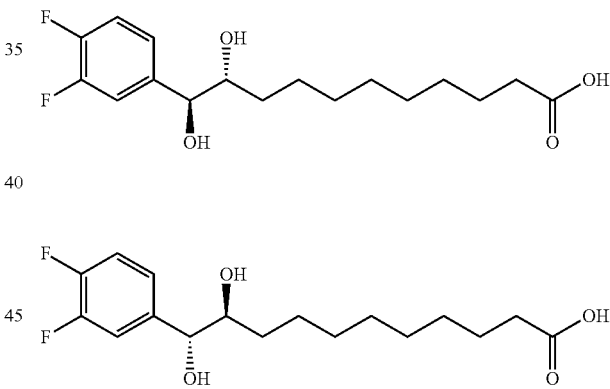

To the solution of (Z)-B7 (361 mg, 1.22 mmol) in t-butanol/water (2/1, 6 mL) was added NMO (494 mg, 4.22 mmol) and osmium tetroxide (2.5 wt % in t-BuOH, 186 μL, 0.0183 mmol). After stirring at room temperature for 20 h, the reaction mixture was quenched with sat. Na$_2$S$_2$O$_3$ (15 mL). The mixture was concentrated and the residue was dissolved in ethyl acetate (50 mL), washed with sat. Na$_2$S$_2$O$_3$ (50 mL), and brine (50 mL), dried over MgSO$_4$, filtered and concentrated. The residue was purified by column chromatography (ethyl acetate/n-hexane=1/2 then 1/1) to afford ant-B21 (246 mg, 0.745 mmol, 61%, a mixture of anti-diol isomers) as colorless oil. $^1$H-NMR (CD$_3$OD, 400 MHz) δ 7.03-7.25 (m, 3H), 4.36 (d, J=5.5 Hz, 1H), 3.47-3.57 (m, 1H), 2.16-2.22 (m, 2H), 1.18-1.56 (m, 14H). $^{13}$C-NMR (CD$_3$OD, 100 MHz) δ 177.73, 151.19 (dd, J=245, 13 Hz), 150.72 (dd, J=245, 13 Hz), 141.46, 124.57, 117.49, 117.08, 77.34, 77.25, 76.42, 76.06, 34.95, 33.75, 33.50, 30.63, 30.51, 30.44, 30.34, 30.20, 26.83, 26.07. HRMS (ESI) calculated for C$_{17}$H$_{24}$F$_2$O$_4$Na [M+Na]$^+$: 353.1540, found: 353.1566.

(4) Synthetic Scheme 4: Synthesis of Compound C5-C7

Synthesis of 3,4-di-O-benzyl-1-O-(6-azido-2,3,4-tri-O-benzyl-6-deoxy-α-D-galactopyranosyl)-2-hexacosanoylamino-D-ribo-octadecan-1,3,4-triol (C1)

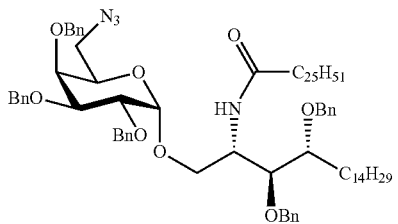

Compound C1 may be synthesized according to Zhou, X. T. et al. *Org Lett* 2002, 4, 1267-1270. Data for C1: $^1$H-NMR (CDCl$_3$, 400 Hz) δ 7.35-7.21 (m, 25H), 5.94 (d, J=6.0 Hz, 1H), 4.95 (d, J=11.4 Hz, 1H), 4.82 (d, J=3.2 Hz, 1H), 4.79-4.91 (m, 4H), 4.63-4.55 (m, 3H), 4.37-4.48 (m, 2H), 4.18-4.30 (m, 2H), 4.00 (dd, J=3.6, 10.1 Hz, 1H), 3.87-3.81 (m, 7H), 3.52-3.50 (m, 1H), 1.78-1.79 (m, 74H), 0.86 (t, J=7.0 Hz, 6H).

Synthesis of 1-O-(6-phenylacetamido-6-deoxy-α-D-galactopyranosyl)-2-hexacosanoylamino-D-ribo-octadecan-1,3,4-triol (C5)

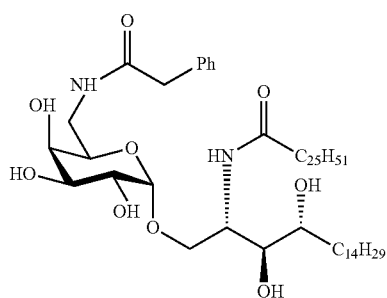

To the solution of C1 (24 mg, 0.018 mmol) in THF/water (10/1, 5 mL) was added triphenylphosphine (10 mg, 0.038 mmol). After stirring at room temperature for 2 days, the mixture was concentrated and dried in vacuum. The residue was dissolved in chloroform (3 mL). Phenylacetic acid (3 mg, 0.02 mmol), NMM (5 μL, 0.05 mmol) and HBTU (10 mg, 0.026 mmol) were added to this solution. After stirring at room temperature for 12 h, the mixture was concentrated and purified by column chromatography (ethyl acetate/n-hexane=1/8 to 1/6 to 1/4) to give compound C2. The resulting intermediate of C2 was dissolved in dichloromethane/methanol (1/1, 5 mL) and Pd(OH)$_2$ (5.0 mg) was then added. After stirring at room temperature under hydrogen for 15 h, the mixture was filtered through Celite pad and washed with dichloromethane/methanol (1/1). The filtrate was concentrated and purified by column chromatography (dichloromethane/methanol=1/1) to afford C5 (4.0 mg, 0.004 mmol, 22%) as white wax. $^1$H-NMR (pyridine-d$_5$, 400 Hz) δ 7.24-7.43 (m, 5H), 5.51 (d, J=3.8 Hz, 1H), 4.50-4.67 (m, 2H), 4.09-4.51 (m, 8H), 3.89 (s, 2H), 3.82-4.01 (m, 1H), 2.21-2.57 (m, 4H), 1.08-1.96 (m, 74H), 0.88 (t, J=6.1 Hz, 6H). $^{13}$C-NMR (pyridine-d$_5$, 150 Hz) δ 173.75, 173.46, 142.53, 129.24, 129.20, 126.75, 101.71, 77.08, 72.95, 71.64, 71.34, 70.91, 70.50, 68.82, 51.89, 41.50, 38.77, 37.20, 34.81, 32.67, 32.51, 30.78, 30.55, 30.42, 30.39, 30.32, 30.20, 29.99, 26.90, 26.79, 23.32, 14.66. [α]$_D^{25}$ +39.3 (c 1.0, CH$_2$Cl$_2$/CH$_3$OH: 1/1). LRMS (ESI) calculated for C$_{58}$H$_{107}$N$_2$O$_9$[M+H]$^+$: 975.80, found: 975.67.

Synthesis of 1-O-(6-(3-phenylpropylamido)-6-deoxy-α-D-galactopyranosyl)-2-hexacosanoylamino-D-ribo-octadecan-1,3,4-triol (C6)

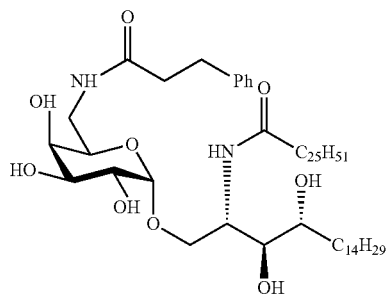

By the similar procedure of synthesis of C5, compound C1 (24 mg, 0.018 mmol) and 3-phenylpropanoic acid (2.2 mg, 0.018 mmole) were used as starting materials to afford C6 (10 mg, 0.010 mmol, 55%). $^1$H-NMR (pyridine-d$_5$, 400 Hz) δ 7.29-7.30 (m, 5H), 5.50 (d, J=3.7 Hz, 1H), 5.20-5.30 (m, 1H), 4.56-4.65 (m, 2H), 4.48 (t, J=6.6 Hz, 1H), 4.25-4.38 (m, 5H), 4.15-4.23 (m, 1H), 3.86-3.95 (m, 1H), 3.17-3.26 (m, 2H), 2.74-2.89 (m, 2H), 2.41-2.55 (m, 2H), 1.08-2.04 (m, 74H), 0.89 (t, J=6.7 Hz, 3H). $^{13}$C-NMR (pyridine-d$_5$, 400 Hz) δ 173.81, 173.52, 149.78, 142.60, 129.32, 129.27, 126.83, 101.78, 77.15, 73.00, 71.70, 71.41, 70.98, 70.56, 68.88, 51.94, 38.84, 37.26, 34.88, 32.74, 32.58, 30.86, 30.63, 20.50, 30.47, 30.39, 26.97, 26.87, 23.40, 14.74. [α]$_D^{25}$ +36.0 (c 1.0, CH$_2$Cl$_2$/CH$_3$OH: 1/1). LRMS (ESI) calculated for C$_{59}$H$_{109}$N$_2$O$_9$ [M+H]$^+$: 989.81, found: 989.60.

Synthesis of 1-O-(6-(4-phenylbutylamido)-6-deoxy-α-D-galactopyranosyl)-2-hexacosanoylamino-D-ribo-octadecan-1,3,4-triol (C7)

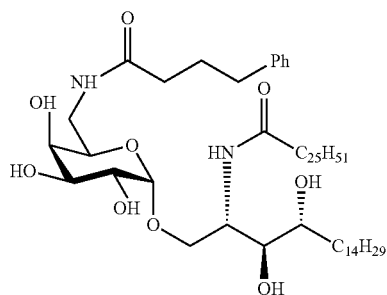

By the similar procedure of synthesis of C5 compound C1 (24 mg, 0.018 mmol) and 4-phenylbutanoic acid (2.0 mg, 0.018 mmole) were used as starting materials to afford C7

(9.0 mg, 0.090 mmol, 50%). $^1$H-NMR (pyridine-$d_5$, 400 Hz) 67.27-7.40 (m, 5H), 5.50 (d, J=3.7 Hz, 1H), 5.21-5.27 (m, 1H), 4.55-4.66 (m, 2H), 4.48 (t, J=6.6 Hz, 1H), 4.25-4.37 (m, 6H), 4.15-4.23 (m, 1H), 3.87-3.95 (m, 1H), 3.16-3.25 (m, 2H), 2.74-2.89 (m, 2H), 2.41-2.55 (m, 2H), 1.02-1.98 (m, 74H), 0.88 (t, J=7.2 Hz, 6H). $^{13}$C-NMR (pyridine-$d_5$, 400 Hz) δ 173.30, 173.02, 142.07, 128.82, 128.70, 126.33, 101.28, 76.66, 72.50, 71.19, 70.90, 70.48, 70.05, 68.39, 51.44, 41.06, 38.34, 36.77, 34.38, 32.25, 32.10, 30.37, 30.13, 30.01, 29.98, 29.91, 29.79, 29.76, 29.59, 29.58, 26.47, 26.37, 22.91, 14.25. $[\alpha]_D^{25}$ +36.9 (c 1.0, $CH_2Cl_2/CH_3OH$: 1/1). LRMS (ESI) calculated for $C_{60}H_{111}N_2O_9[M+H]^+$: 1003.83, found: 1003.47.

(5) Synthetic Scheme 5: Synthesis of Compound C20-C31

Synthesis of 1-O-(6-O-toluenesulfonyl-α-D-galactopyranosyl)-2-(11-(3,4-difluorophenyl)undecanoyl) amino-D-ribo-1,3,4-octadecantriol (C17)

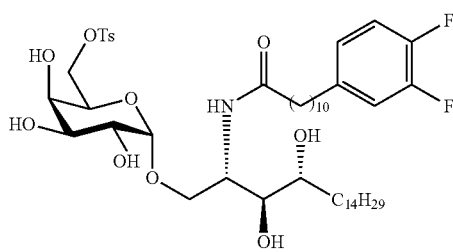

To the solution of A15 (2.58 g, 3.40 mmol) in pyridine (30 mL) was added the solution of p-toluenesulfonyl chloride (712 mg, 3.74 mmol) in pyridine (20 mL) in an ice bath. The reaction mixture was returned to rt. After stirring for 16 h, the solvent was evaporated and the residue was purified by column chromatography (dichloromethane/methanol=100/1 to 50/1 to 20/1 to 15/1) to afford C17 as yellow wax (782 mg, 0.855 mmol, 25%, 100% BRSM with 2.01 g starting material recovery). $^1$H-NMR ($CD_3OD/CDCl_3$=1/1, 400 MHz) δ 7.96 (d, J=8.3 Hz, 2H), 7.56 (d, J=8.1 Hz, 2H), 7.10-7.27 (m, 2H), 7.02-7.09 (m, 1H), 5.01 (d, J=3.2 Hz, 1H), 4.29-4.42 (m, 3H), 4.21 (t, J=5.9 Hz, 1H), 3.96-4.04 (m, 2H), 3.85-3.95 (m, 2H), 3.81 (dd, J=4.0, 10.6 Hz, 1H), 3.70-3.76 (m, 2H), 2.74 (t, J=7.6 Hz, 2H), 2.62 (s, 3H), 2.35-2.43 (m, 2H), 1.67-1.88 (m, 4H), 1.36-1.60 (m, 38H), 1.05 (t, J=6.7 Hz, 3H). $^{13}$C-NMR ($CD_3OD/CDCl_3$=1/1, 100 MHz) δ173.84, 149.47 (dd, J=246, 13 Hz), 148.00 (dd, J=244, 13 Hz), 144.74, 139.43, 132.04, 129.32, 127.44, 123.60, 116.22, 114.55, 99.09, 73.87, 71.39, 69.27, 68.98, 68.51, 68.15, 68.07, 66.95, 35.85, 34.46, 31.71, 31.34, 30.72, 29.21, 29.17, 29.12, 29.06, 28.96, 28.91, 28.82, 28.77, 28.50, 25.30, 22.06, 20.67, 13.22. HRMS (ESI) calculated for $C_{48}H_{78}F_2NO_{11}S$ $[M+H]^+$: 914.5264, found: 914.5228.

Synthesis of 1-O-(6-azido-6-deoxy-α-D-galactopyranosyl)-2-(11-(3,4-difluorophenyl)undecanoyl)amino-D-ribo-1,3,4-octadecantriol (C18)

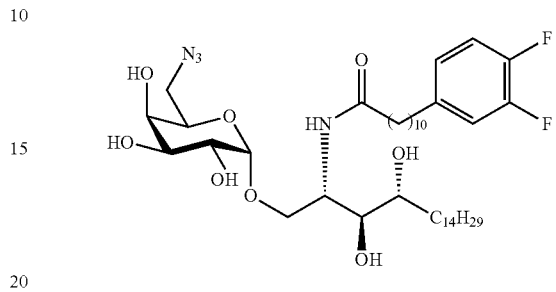

To the solution of C17 (1.63 g, 1.78 mmol) in DMF (15 mL) was added sodium azide (322 mg, 4.95 mmol). The reaction mixture was stirred at 100° C. for 2 days. The mixture was concentrated and the residue was purified by column chromatography (dichloromethane/methanol=20/1 to 15/1) to afford crude C18 (1.15 g, 1.47 mmol, 82%) as yellow solids. mp: 101° C. $^1$H-NMR ($CD_3OD/CDCl_3$=1/1, 400 MHz) δ 7.25-7.51 (m, 3H), 5.36 (d, J=3.2 Hz, 1H), 4.57-4.67 (m, 1H), 4.12-4.42 (m, 6H), 3.94-4.06 (m, 3H), 3.74 (dd, J=12.8, 4.8 Hz, 1H), 3.00 (t, J=7.7 Hz, 2H), 2.60-2.67 (m, 2H), 1.62-2.15 (m, 42H), 1.32 (t, J=6.8 Hz, 3H). HRMS (ESI) calculated for $C_{41}H_{71}F_2N_4O_8$ $[M+H]^+$: 785.5240, found: 785.5267.

Synthesis of 1-O-(6-amino-6-deoxy-α-D-galactopyranosyl)-2-(11-(3,4-difluorophenyl)undecanoyl) amino-D-ribo-1,3,4-octadecantriol (C19)

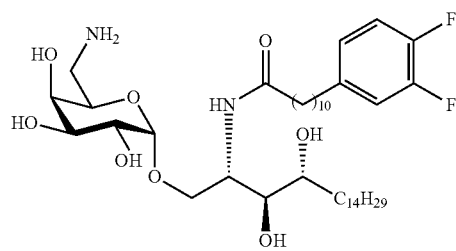

The solution of C18 (1.11 g, 1.41 mmol) in THF/water (10/1, 33 mL) was added triphenylphosphine (0.74 g, 2.8 mmol). The reaction mixture was stirred at room temperature for 2 days. The mixture was concentrated and the residue was purified by column chromatography (1% triethylamine, dichloromethane/methanol=6/1 to 4/1 to 2/1) to afford C19 (566 mg, 0.746 mmol, 53%) as white solids. mp: 161° C. $^1$H-NMR ($CD_3OD$, 400 MHz) δ 6.95-7.09 (m, 2H), 6.86-6.88 (m, 1H), 4.82 (d, J=3.2 Hz, 1H), 4.13-4.19 (m, 1H), 3.83 (dd, J=10.4, 4.4 Hz, 1H), 3.75 (d, J=2.0, 1H), 3.63-3.73 (m, 3H), 3.59 (dd, J=10.8, 5.6 Hz, 1H), 3.44-3.54 (m, 2H), 2.87 (dd, J=13.2, 7.6 Hz, 1H), 2.72 (dd, J=13.2, 4.4 Hz, 1H), 2.51 (t, J=7.6 Hz, 2H), 2.14 (t, J=7.5 Hz, 2H), 1.50-1.63 (m, 4H), 1.16-1.32 (m, 38H), 0.82 (t, J=6.8 Hz, 3H). $^{13}$C-NMR ($CD_3OD$, 100 MHz) δ 176.07, 151.5 (d, J=246, 13 Hz), 150.8 (d, J=243, 12 Hz), 141.74, 125.79, 118.16, 118.02, 101.43, 75.90, 73.12, 72.46, 72.02, 71.63, 70.33, 68.35, 52.18, 43.44, 37.46, 36.20, 33.37, 33.26, 32.68, 31.06, 31.02, 30.96, 30.89, 30.81, 30.73, 30.67, 30.62, 30.39, 27.30, 27.21, 23.29. HRMS (ESI) calculated for $C_{41}H_{73}F_2N_2O_8$ [M+H]$^+$: 759.5335, found: 759.5319.

Synthesis of 1-O-(6-(4-Nitrophenylacetamido)-6-deoxy-α-D-galactopyranosyl)-2-(11-(3,4-difluorophenyl)undecanoyl)amino-D-ribo-1,3,4-octadecantriol (C20)

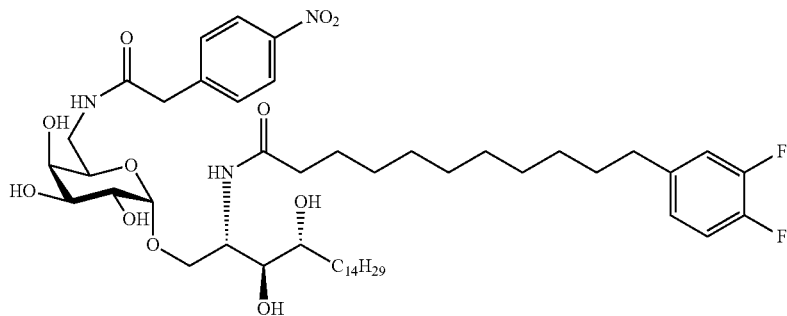

To the solution of C19 (34 mg, 0.045 mmol) in dichloromethane/methanol (1/1, 3 mL) was added 4-nitrophenylacetic acid (8.1 mg, 0.045 mmol), HBTU (34 mg, 0.090 mmol) and NMM (20 μL, 0.18 mmol). After stirring at room temperature for 16 h, the mixture was concentrated and purified by column chromatography (dichloromethane/methanol=30/1 to 20/1). The crude product was dissolved in dichloromethane/methanol (1/1, 3 mL) and Si-carbonate silica gel (HOBT scavenger, 100 mg) was added to the solution. After stirring at room temperature for 1 h, the mixture was filtered and washed with dichloromethane/methanol (1/1). The filtrate was concentrated and dried in vacuum to afford C20 (13 mg, 0.014 mmol, 31%) as light yellow wax. $^1$H-NMR (CDCl$_3$/CD$_3$OD=1/1, 200 MHz) δ 8.25 (d, J=8.7 Hz, 2H), 7.68 (d, J=8.7 Hz, 2H), 6.90-7.21 (m, 3H), 4.94 (d, J=3.2 Hz, 1H), 4.20-4.26 (m, 1H), 3.77-3.92 (m, 5H), 3.58-3.74 (m, 6H), 2.63 (t, J=7.4 Hz, 2H), 2.28 (t, J=7.6 Hz, 2H), 1.30-1.81 (m, 42H), 0.98 (t, J=6.8 Hz, 3H). $^{13}$C-NMR (CDCl$_3$/CD$_3$OD=1/1, 50 MHz) δ 173.93, 170.81, 149.17 (dd, J=246, 13 Hz), 148.05 (dd, J=244, 13 Hz), 146.43, 142.53, 139.35, 129.58, 123.59, 122.95, 116.28, 116.11, 98.99, 73.65, 71.21, 69.35, 69.18, 68.41, 68.14, 66.16, 49.81, 41.69, 39.69, 36.34, 35.69, 34.36, 31.61, 31.25, 30.66, 29.04, 28.74, 28.41, 25.27, 21.97, 13.07. $[α]_D^{25}$ +39.3 (c 1.0, CH$_2$Cl$_2$/CH$_3$OH: 1/1). HRMS (ESI) calculated for $C_{49}H_{78}F_2N_3O_{11}$ [M+H]$^+$: 922.5604, found: 922.5629.

Synthesis of 1-O-(6-(2,4-dinitrophenylacetamido)-6-deoxy-α-D-galactopyranosyl)-2-(11-(3,4-difluorophenyl)undecanoyl)amino-D-ribo-1,3,4-octadecantriol (C21)

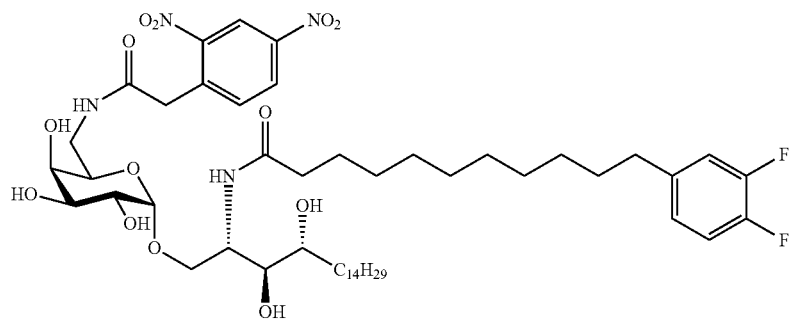

By the similar procedure of synthesis of C20, compound C19 (34 mg, 0.045 mmol) and 2,4-dinitrophenylacetic acid (10 mg, 0.045 mmole) were used as starting materials to afford C21 (4.0 mg with inseparable impurities, 0.0041 mmol, 9%). $^1$H-NMR (CDCl$_3$/CD$_3$OD=1/1, 600 MHz) δ 7.39-7.48 (m, 3H), 6.97-7.17 (m, 3H), 4.98 (d, J=3.2 Hz, 1H), 4.24-4.31 (m, 1H), 3.59-3.93 (m, 10H), 2.65 (t, J=7.4 Hz, 2H), 2.26-2.31 (m, 2H), 1.14-1.87 (m, 42H), 0.90-1.02 (m, 3H). $^{13}$C-NMR (CDCl$_3$/CD$_3$OD=1/1, 150 MHz) δ 173.95, 169.65, 148.64, 147.80, 139.33, 134.76, 132.72, 129.90, 129.13, 123.53, 123.15, 116.92, 116.57, 116.13, 110.69, 99.01, 73.64, 73.42, 71.16, 69.32, 69.08, 68.12, 66.07, 49.80, 39.45, 39.60, 38.18, 38.13, 36.30, 35.66, 34.33, 34.30, 33.63, 32.01, 31.60, 31.43, 30.67, 30.58, 29.73, 29.23, 28.39, 28.35, 28.23, 26.30, 25.23, 25.17, 23.06, 22.25, 22.20, 21.78, 12.98. $[α]_D^{25}$ +47.1 (c 1.0, CH$_2$Cl$_2$/CH$_3$OH: 1/1). HRMS (ESI) calculated for C$_{49}$H$_{76}$F$_2$N$_3$O$_{13}$H [M+H]$^+$: 967.5455, found: 967.5485.

1-O-(6-(4-tert-Butylphenylacetamido)-6-deoxy-α-D-galactopyranosyl)-2-(11-(3,4-difluorophenyl)undecanoyl)amino-D-ribo-1,3,4-octadecantriol (C22)

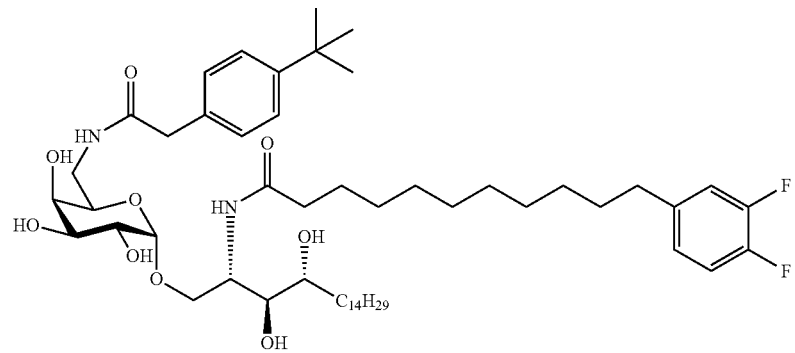

By the similar procedure of synthesis of C20, compound C19 (34 mg, 0.045 mmol) and 4-tert-butylphenylacetic acid (8.6 mg, 0.044 mmole) were used as starting materials to afford C22 (12 mg, 0.013 mmol, 29%). mp: 170° C. $^1$H-NMR (CDCl$_3$/CD$_3$OD=1/1, 400 MHz) δ 7.47 (d, J=8.0 Hz, 2H), 7.32 (d, J=8.0 Hz, 2H), 6.98-7.22 (m, 3H), 4.97 (d, J=3.2 Hz, 1H), 4.29-4.34 (m, 1H), 3.80-3.95 (m, 5H), 3.76 (dd, J=10.8, 4.4 Hz, 1H), 3.61-3.71 (m, 5H), 3.36 (dd, J=7.8, 13.8 Hz, 1H), 2.68 (t, J=7.6 Hz, 2H), 2.33 (t, J=7.6 Hz, 2H), 1.63-1.82 (m, 4H), 1.31-1.53 (m, 47H), 1.00 (t, J=6.5 Hz, 3H). $^{13}$C-NMR (CDCl$_3$/CD$_3$OD=1/1, 100 MHz) δ 173.91, 172.88, 149.40 (dd, J=246, 12 Hz), 148.02 (dd, J=243, 13 Hz), 139.36, 131.28, 124.96, 123.57, 116.21, 116.05, 99.06, 73.79, 71.30, 69.35, 68.97, 68.40, 68.20, 66.42, 49.84, 41.82, 39.39, 35.72, 34.37, 33.66, 31.66, 31.25, 30.65, 30.38, 29.14, 29.09, 29.05, 29.03, 28.97, 28.89, 28.83, 28.75, 28.71, 28.68, 28.42, 25.28, 25.24, 21.96, 13.06. $[α]_D^{25}$ +36.4 (c 1.0, CH$_2$Cl$_2$/CH$_3$OH: 1/1). HRMS (ESI) calculated for C$_{53}$H$_{88}$F$_2$N$_2$O$_9$ [M+H]$^+$: 933.6380, found: 933.6435.

Synthesis of 1-O-(6-(4-bromophenylacetamido)-6-deoxy-α-D-galactopyranosyl)-2-(11-(3,4-difluorophenyl)undecanoyl)amino-D-ribo-1,3,4-octadecantriol (C23)

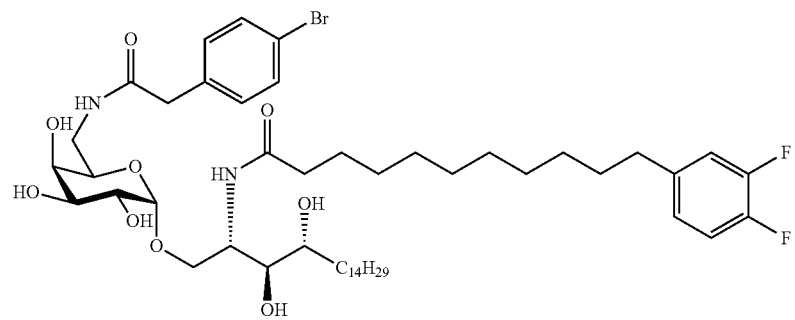

By the similar procedure of synthesis of C20, compound C19 (34 mg, 0.045 mmol) and 4-bromophenylacetic acid (9.7 mg, 0.044 mmole) were used as starting materials to afford C23 (15 mg, 0.016 mmol, 35%) as off-white solids. mp=177° C. $^1$H-NMR (CDCl$_3$/CD$_3$OD=1/1, 400 MHz) δ 7.54 (d, J=8.4 Hz, 2H), 7.29 (d, J=8.0 Hz, 2H), 6.97-7.20 (m, 3H), 4.97 (d, J=3.6 Hz, 1H), 4.28-4.33 (m, 1H), 3.78-3.92 (m, 5H), 3.59-3.74 (m, 6H), 3.37 (dd, J=7.6, 13.6 Hz, 1H), 2.66 (t, J=7.6 Hz, 2H), 2.31 (t, J=7.6 Hz, 2H), 1.30-1.81 (m, 42H), 0.98 (t, J=6.8 Hz, 3H). $^{13}$C-NMR (CDCl$_3$/CD$_3$OD=1/1, 100 MHz) δ 173.90, 171.91, 149.53 (dd, J=247, 13 Hz), 147.86 (dd, J=245, 12 Hz), 139.35, 133.70, 130.98, 130.29, 123.58, 120.22, 120.22, 116.18, 116.02, 99.03, 73.77, 71.26, 69.34, 69.08, 68.38, 68.15, 66.32, 49.81, 41.48, 39.51, 35.68, 34.35, 31.63, 31.23, 30.62, 29.11, 29.08, 29.01, 28.95, 28.87, 28.81, 28.73, 28.68, 28.66, 28.40, 25.25, 25.22, 21.94, 13.03. $[α]_D^{25}$ +42.3 (c 1.0, CH$_2$Cl$_2$/CH$_3$OH: 1/1). HRMS (ESI) calculated for C$_{49}$H$_{78}$BrF$_2$N$_2$O$_9$ [M+H]$^+$: 955.4859, found: 955.4920.

Synthesis of 1-O-(6-(4-methoxyphenylacetamido)-6-deoxy-α-D-galactopyranosyl)-2-(11-(3,4-difluorophenyl)undecanoyl)amino-D-ribo-1,3,4-octadecantriol (C24)

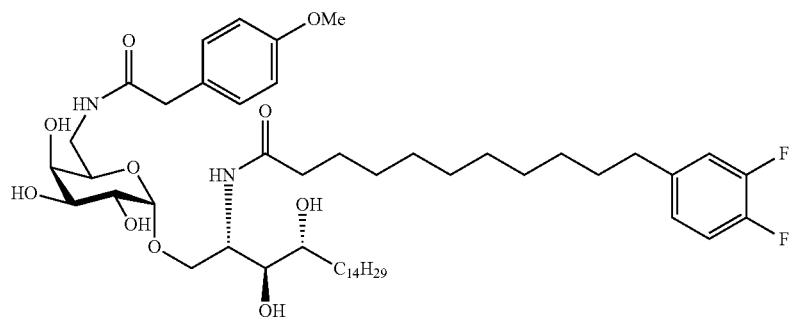

By the similar procedure of synthesis of C20, compound C19 (34 mg, 0.045 mmol) and 4-methoxyphenylacetic acid (7.5 mg, 0.045 mmole) were used as starting materials to afford C24 (15 mg, 0.017 mmol, 38%) as off-white solis. mp: 172° C. $^1$H-NMR (CDCl$_3$/CD$_3$OD=1/1, 400 MHz) δ 7.36 (d, J=8.8 Hz, 2H), 7.12-7.26 (m, 2H), 7.01-7.09 (m, 3H), 5.02 (d, J=3.6 Hz, 1H), 4.32-4.38 (m, 1H), 3.97 (s, 3H), 3.72-3.96 (m, 5H), 3.69-3.78 (m, 4H), 3.65 (s, 2H), 3.40 (dd, J=7.8, 14.0 Hz, 1H), 2.74 (t, J=7.6 Hz, 2H), 2.38 (t, J=7.6 Hz, 2H), 1.38-1.89 (m, 42H), 1.05 (t, J=6.8 Hz, 3H). $^{13}$C-NMR (CDCl$_3$/CD$_3$OD=1/1, 100 MHz) δ 173.91, 173.06, 149.59 (dd, J=247, 13 Hz), 148.08 (dd, J=244, 13 Hz), 158.27, 129.40, 129.66, 126.43, 123.61, 116.29, 116.12, 114.55, 113.62, 99.08, 73.92, 71.39, 61.41, 69.03, 68.41, 68.24, 66.43, 54.47, 49.78, 41.57, 39.46, 35.82, 34.46, 31.80, 31.33, 30.71, 29.22, 29.17, 29.12, 29.11, 29.05, 28.96, 28.90, 28.82, 28.78, 28.75, 28.49, 25.34, 25.31, 22.04, 13.19. $[α]_D^{25}$ +44.3 (c 1.0, CH$_2$Cl$_2$/CH$_3$OH: 1/1). HRMS (ESI) calculated for C$_{50}$H$_{81}$F$_2$N$_2$O$_{10}$ [M+H]$^+$: 907.5859, found: 907.5890.

Synthesis of 1-O-(6-(3,4-di(trifluoromethyl)phenylacetamido)-6-deoxy-α-D-galactopyranosyl)-2-(11-(3,4-ifluorophenyl)undecanoyl)amino-D-ribo-1,3,4-oct adecantriol (C25)

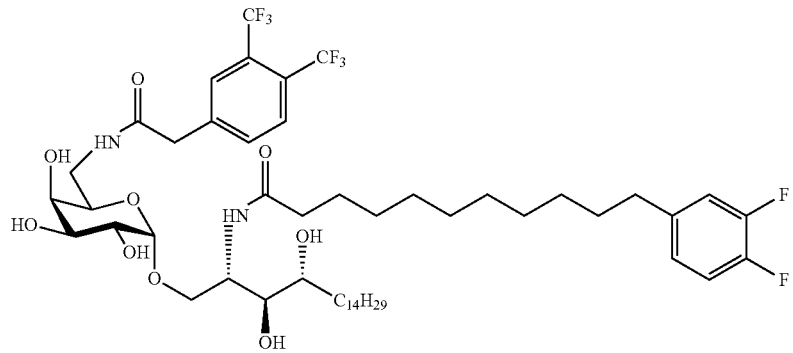

By the similar procedure of synthesis of C20, compound C19 (34 mg, 0.045 mmol) and 3,4-di(trifluororomethanyl)phenylacetic acid (12 mg, 0.045 mmole) were used as starting materials to afford C25 (11 mg, 0.011 mmol, 24%) as off-white solids. mp: 180° C. $^1$H-NMR (CDCl$_3$/CD$_3$OD=1/1, 400 MHz) δ 7.98 (s, 2H), 7.91 (s, 1H), 769-7.22 (m, 3H), 5.01 (d, J=3.6 Hz, 1H), 4.28-4.33 (m, 1H), 3.84-3.99 (m, 5H), 3.83 (s, 2H), 3.78 (dd, J=4.2, 10.8 Hz, 1H), 3.22-3.32 (m, 3H), 3.42-3.51 (m, 1H), 2.69 (t, J=7.6 Hz, 2H), 2.33 (t, J=7.4 Hz, 2H), 1.39-1.82 (m, 42H), 1.00 (t, J=6.8 Hz, 3H). ($^{13}$C-NMR CDCl$_3$/CD$_3$OD=1/1, 100 MHz) δ 174.04, 170.56, 143.17, 139.37, 137.65, 131.13, 130.80, 129.10, 124.18, 123.56, 121.47, 120.09, 116.22, 116.06, 114.50, 99.07, 73.77, 71.32, 69.40, 69.27, 68.42, 68.20, 66.30, 49.99, 41.14, 39.78, 35.75, 34.39, 31.73, 31.27, 30.66, 29.14, 29.09, 29.04, 28.99, 28.88, 28.75, 28.71, 28.69, 28.42, 25.29, 25.24, 21.98, 13.08. $[\alpha]_D^{25}$ +40.1 (c 1.0, CH$_2$Cl$_2$/CH$_3$OH: 1/1). HRMS (ESI) calculated for C$_{51}$H$_{77}$F$_8$N$_2$O$_9$ [M+H]$^+$: 1013.5501, found: 1013.5567.

Synthesis of 1-O-(6-(3,4-difluorophenylacetamido)-6-deoxy-α-D-galactopyranosyl)-2-(11-(3,4-difluorophenyl)undecanoyl)amino-D-ribo-1,3,4-octadecantriol (C26)

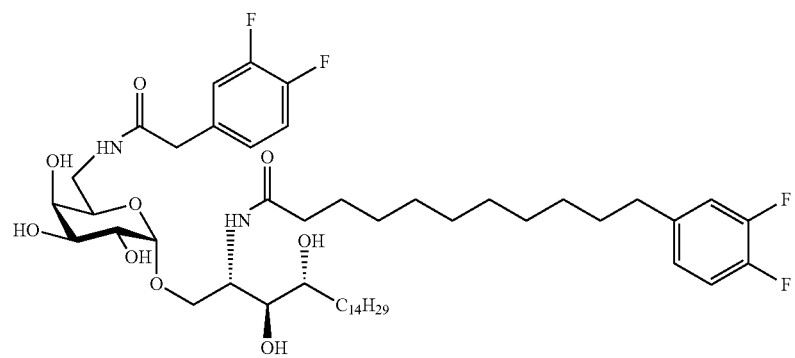

By the similar procedure of synthesis of C20, compound C19 (34 mg, 0.045 mmol) and 3,4-difluorophenylacetic acid (7.7 mg, 0.045 mmole) were used as starting materials to afford C26 (17 mg, 0.019 mmol, 42%) as off-white solids. mp: 182° C. $^1$H-NMR (CDCl$_3$/CD$_3$OD=1/1, 400 MHz) δ 6.97-7.43 (m, 6H), 4.97 (d, J=3.6 Hz, 1H), 4.28 (q, J=4.4, 9.6 Hz, 1H), 3.83-4.01 (m, 4H), 3.80 (dd, J=3.2, 10.0 Hz, 1H), 3.71 (dd, J=4.4, 10.6 Hz, 1H), 3.60-3.68 (m, 3H), 3.59 (s, 2H), 3.38 (dd, J=8.0, 13.6 Hz, 1H), 2.66 (t, J=7.6 Hz, 2H), 2.30 (t, J=7.6 Hz, 2H), 1.32-1.81 (m, 42H), 0.97 (t, J=6.8 Hz, 3H). $^{13}$C-NMR CDCl$_3$/CD$_3$OD=1/1, 100 MHz) δ 173.92, 171.63, 150.67, 150.03, 149.13, 148.25, 147.65, 146.72, 139.34, 131.81, 124.72, 123.54, 117.52, 117.34, 116.97, 116.59, 116.42, 116.25, 116.08, 115.93, 99.02, 73.75, 71.23, 69.34, 69.15, 68.38, 68.14, 66.24, 49.82, 41.06, 39.57, 35.66, 34.33, 31.63, 31.23, 30.61, 29.10, 29.07, 29.00, 28.94, 28.85, 28.79, 28.71, 28.65, 28.38, 25.24, 25.20, 21.93, 13.01. $[\alpha]_D^{25}$ +53.8 (c 1.0, CH$_2$Cl$_2$/CH$_3$OH: 1/1). HRMS (ESI) calculated for C$_{49}$H$_{77}$F$_4$N$_2$O$_9$ [M+H]$^+$: 913.5565, found: 913.5606.

Synthesis of 1-O-(6-(3-trifluoromethylphenyl-acetamido)-6-deoxy-α-D-galactopyranosyl)-2-(11-(3,4-difluorophenyl)undecanoyl)amino-D-ribo-1,3,4-octadecantriol (C27)

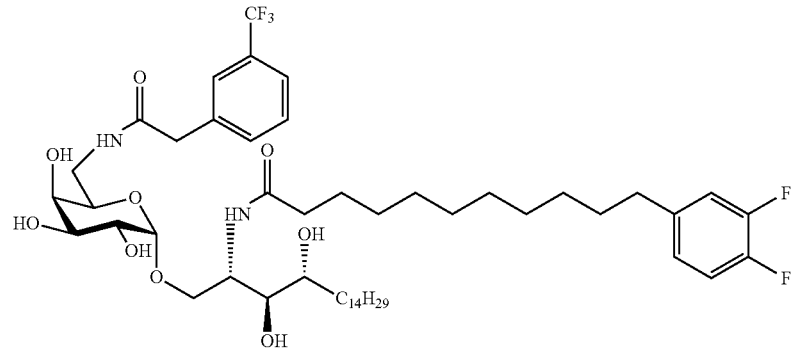

By the similar procedure of synthesis of C20, compound C19 (34 mg, 0.045 mmol) and 3-trifluoromethylphenylacetic acid (9.2 mg, 0.045 mmole) were used as starting materials to afford C27 (12 mg, 0.013 mmol, 29%) as off-white solids. mp: 157° C. $^1$H-NMR (CDCl$_3$/CD$_3$OD=1/1, 400 MHz) δ 6.96-7.82 (m, 7H), 4.96 (d, J=3.6 Hz, 1H), 4.25-4.30 (m, 1H), 4.03-4.10 (m, 1H), 3.77-3.91 (m, 5H), 3.53-3.74 (m, 5H), 3.36-3.44 (m, 1H), 2.65 (t, J=7.6 Hz, 2H), 2.29 (t, J=7.6 Hz, 2H), 1.27-1.76 (m, 42H), 0.97 (t, J=6.8 Hz, 3H). $^{13}$C-NMR (CDCl$_3$/CD$_3$OD=1/1, 100 MHz) δ 174.52, 172.19, 150.04 (dd, J=247, 13 Hz), 148.52 (dd, J=244, 13 Hz), 139.90, 136.43, 132.64, 129.02, 127.67, 125.80, 124.17, 116.76, 116.60, 111.27, 99.64, 74.33, 71.87, 69.93, 69.73, 68.98, 68.76, 66.90, 60.57, 50.44, 42.27, 40.16, 36.25, 34.92, 32.20, 31.82, 31.21, 29.68, 29.65, 29.59, 29.53, 29.44, 29.38, 29.30, 29.24, 28.97, 25.83, 25.80, 22.52, 13.60. $[α]_D^{25}$ +47.4 (c 1.0, CH$_2$Cl$_2$/CH$_3$OH: 1/1). HRMS (ESI) calculated for C$_{50}$H$_{78}$F$_5$N$_2$O$_9$ [M+H]$^+$: 945.5627, found: 945.5611.

Synthesis of 1-O-(6-(4-methylphenylacetamido)-6-deoxy-α-D-galactopyranosyl)-2-(11-(3,4-difluorophenyl)undecanoyl)amino-D-ribo-1,3,4-octadecantriol (C28)

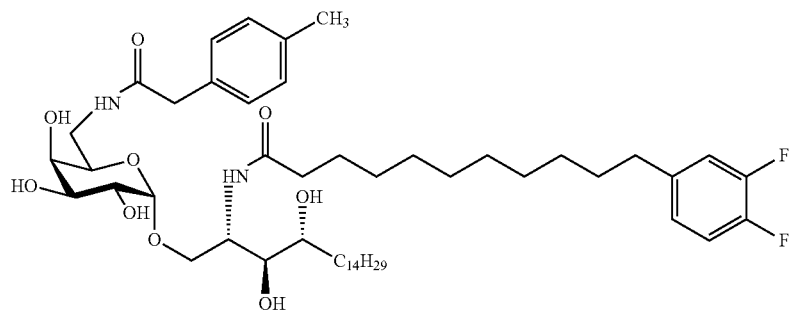

By the similar procedure of synthesis of C20, compound C19 (34 mg, 0.045 mmol) and 4-methylphenylacetic acid (6.8 mg, 0.045 mmole) were used as starting materials to afford C28 (11 mg, 0.012 mmol, 27%) as off-white solids. mp: 171° C. $^1$H NMR (CDCl$_3$/CD$_3$OD=1/1, 400 MHz) δ 7.28-44 (m, 4H), 7.12-7.26 (m, 2H), 7.03-7.08 (m, 1H), 5.01 (d, J=3.6 Hz, 1H), 4.32-4.41 (m, 1H), 3.83-3.95 (m, 5H), 3.67-3.79 (m, 3H), 3.66 (s, 2H), 3.40 (dd, J=7.6, 13.6 Hz, 1H), 2.73 (t, J=7.6 Hz, 2H), 2.37 (t, J=7.6 Hz, 2H), 1.32-1.87 (m, 42H), 1.05 (t, J=6.8 Hz, 3H). $^{13}$C-NMR (CDCl$_3$/CD$_3$OD=1/1, 100 MHz) δ 173.94, 172.96, 149.83 (dd, J=247, 13 Hz), 148.02 (dd, J=244, 13 Hz), 139.42, 136.24, 131.26, 128.86, 128.47, 123.42, 116.31, 116.15, 99.10, 73.89, 71.43, 69.40, 68.98, 68.41, 68.25, 66.49, 49.82, 42.07, 39.42, 35.83, 34.47, 31.78, 31.34, 30.73, 29.23, 29.19, 29.12, 29.06, 28.97, 28.92, 28.84, 28.80, 28.77, 28.51, 25.35, 25.32, 22.06, 20.10, 13.22. $[α]_D^{25}$ +31.8 (c 1.0, CH$_2$Cl$_2$/CH$_3$OH: 1/1). HRMS (ESI) calculated for C$_{50}$H$_{81}$F$_2$N$_2$O$_9$ [M+H]$^+$: 891.5910, found: 891.5988.

Synthesis of 1-O-(6-(3-methylphenylacetamido)-6-deoxy-α-D-galactopyranosyl)-2-(11-(3,4-difluorophenyl)undecanoyl)amino-D-ribo-1,3,4-octadecantriol (C29)

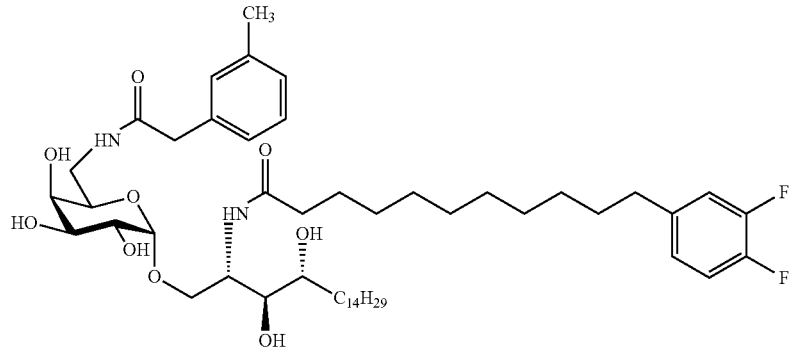

By the similar procedure of synthesis of C20, compound C19 (34 mg, 0.045 mmol) and 3-methylphenylacetic acid (6.8 mg, 0.045 mmole) were used as starting materials to afford C29 (14 mg, 0.016 mmol, 35%) as off-white solids. mp: 167° C. $^1$H-NMR (CDCl$_3$/CD$_3$OD=1/1, 400 MHz) δ 7.18-7.51 (m, 7H), 5.08 (d, J=4.0 Hz, 1H), 4.36-4.43 (m, 1H), 3.91-4.02 (m, 5H), 3.23-3.35 (m, 4H), 3.73 (s, 2H), 3.47 (dd, J=7.8, 13.8 Hz, 1H), 2.79 (t, J=7.8 Hz, 2H), 2.57 (s, 3H), 2.43 (t, J=7.6 Hz, 2H), 1.46-1.94 (m, 42H), 1.11 (t, J=6.8 Hz, 3H). $^{13}$C NMR (CDCl$_3$/CD$_3$OD=1/1, 100 MHz) δ 173.96, 172.85, 149.52 (dd, J=245, 13 Hz), 148.13 (dd, J=243, 13 Hz), 139.43, 137.90, 134.27, 129.41, 128.13, 127.37, 125.61, 123.67, 116.35, 116.19, 99.15, 73.99, 71.49, 69.44, 69.00, 68.41, 68.30, 66.53, 49.88, 42.50, 39.46, 35.89, 34.52, 31.91, 31.39, 30.76, 29.28, 29.23, 29.11, 29.01, 28.96, 28.88, 28.84, 28.81, 28.55, 25.38, 25.36, 22.11, 13.29. [α]$_D^{25}$ +36.8 (c 1.0, CH$_2$Cl$_2$/CH$_3$OH: 1/1). HRMS (ESI) calculated for C$_{50}$H$_{81}$F$_2$N$_2$O$_9$ [M+H]$^+$: 891.5910, found: 891.5950.

Synthesis of 1-O-(6-(2-methylphenylacetamido)-6-deoxy-α-D-galactopyranosyl)-2-(11-(3,4-difluorophenyl)undecanoyl)amino-D-ribo-1,3,4-octadecantriol (C30)

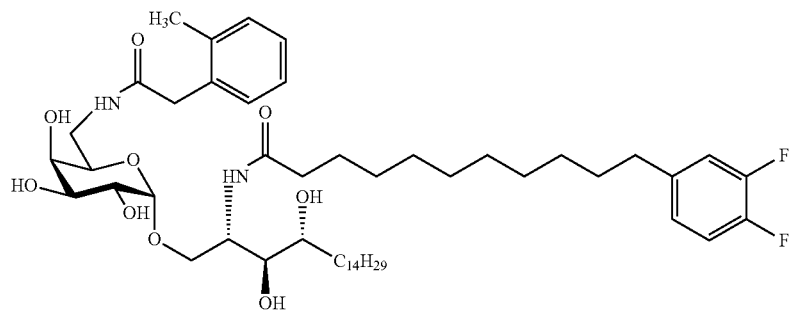

By the similar procedure of synthesis of C20, compound C19 (34 mg, 0.045 mmol) and 2-methylphenylacetic acid (6.8 mg, 0.045 mmole) were used as starting materials to afford C30 (16 mg, 0.018 mmol, 40%) as off-white solids. mp: 182° C. $^1$H-NMR (CDCl$_3$/CD$_3$OD=1/1, 400 MHz) δ 7.31-7.37 (m, 4H), 7.01-7.26 (m, 3H), 4.99 (d, J=3.6 Hz, 1H), 4.30-4.35 (m, 1H), 3.83-3.94 (m, 5H), 3.68-3.75 (m, 6H), 3.40 (dd, J=8.0, 13.8 Hz, 1H), 2.72 (t, J=7.8 Hz, 2H), 2.45 (s, 3H), 2.36 (t, J=7.6 Hz, 2H), 1.32-1.87 (m, 42H), 1.04 (t, J=6.8 Hz, 3H). $^{13}$C-NMR (CDCl$_3$/CD$_3$OD=1/1, 100 MHz) δ 173.86, 172.42, 149.48 (dd, J=246, 13 Hz), 147.94 (dd, J=243, 13 Hz), 139.41, 136.38, 132.67, 129.91, 129.65, 126.99, 125.79, 123.63, 116.28, 116.11, 99.15, 73.91, 71.38, 69.38, 69.11, 68.35, 68.20, 66.56, 49.74, 40.27, 39.49, 35.80, 34.45, 31.78, 31.32, 30.70, 29.21, 29.16, 29.10, 29.04, 28.95, 28.90, 28.81, 28.77, 28.74, 28.48, 25.33, 25.29, 22.03, 18.65, 13.17. [α]$_D^{25}$ +38.3 (c 1.0, CH$_2$Cl$_2$/CH$_3$OH: 1/1). HRMS (ESI) calculated for C$_{50}$H$_{81}$F$_2$N$_2$O$_9$ [M+H]$^+$: 891.5910, found: 891.5987.

Synthesis of 1-O-(6-(2-naphthylacetamido)-6-deoxy-α-D-galactopyranosyl)-2-(11-(3,4-difluorophenyl)undecanoyl)amino-D-ribo-1,3,4-octadecantriol (C31)

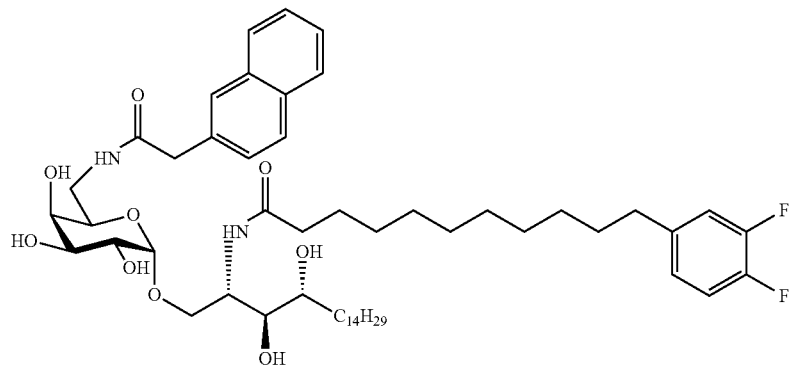

By the similar procedure of synthesis of C20, compound C19 (34 mg, 0.045 mmol) and 2-naphthylacetic acid (8.4 mg, 0.045 mmole) were used as starting materials to afford C31 (12 mg, 0.013 mmol, 29%) as white solid. mp: 178° C. $^1$H-NMR (CDCl$_3$/CD$_3$OD=1/1, 400 MHz) δ 7.85-8.04 (m, 3H), 7.40-7.69 (m, 4H), 7.05-7.29 (m, 3H), 5.03 (d, J=3.6 Hz, 1H), 4.31-4.40 (m, 1H), 3.87-4.01 (m, 6H), 3.72-3.81 (m, 4H), 3.46 (dd, J=7.8, 14.0 Hz, 1H), 2.76 (t, J=7.6 Hz, 2H), 2.38 (t, J=8.0 Hz, 2H), 1.32-1.90 (m, 42H), 1.08 (t, J=6.6 Hz, 3H). $^{13}$C-NMR (CDCl$_3$/CD$_3$OD=1/1, 150 MHz) δ 173.92, 172.58, 149.54 (dd, J=244, 12 Hz), 147.93 (dd, J=240, 13 Hz), 142.73, 139.39, 133.06, 131.96, 127.78, 127.34, 127.01, 126.97, 126.48, 125.61, 125.20, 123.60, 123.30, 123.14, 117.04, 116.24, 116.09, 110.83, 99.07, 73.85, 71.38, 69.38, 69.05, 68.42, 68.21, 66.45, 49.81, 42.35, 39.52, 35.75, 34.41, 31.74, 31.29, 30.67, 29.72, 29.18, 29.13, 29.07, 29.01, 28.92, 28.68, 28.78, 28.72, 28.45, 25.30, 25.28, 22.00, 13.12. $[α]_D^{25}$ +8.3 (c 1.0, CH$_2$Cl$_2$/CH$_3$OH: 1/1).

Synthesis of Compounds of Formula (1)

A number of glycosphingolipids were synthesized and tested for NKT cell activation. Compounds' structures are according to formula 1.

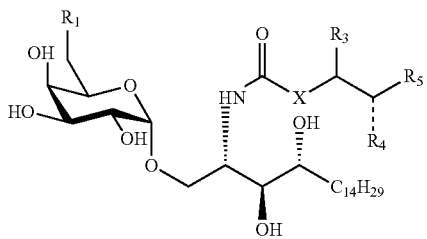

wherein compound No. (R) is selected from Table 1 to provide the corresponding compounds.

TABLE 1

| Compound structure. | Compound no., R = |
|---|---|
| | A15: X = OPh, Y = H, Z = H<br>A16: X = O-i-Pr, Y = H, Z = H<br>A17: X = F, Y = F, Z = H<br>A18: X = F, Y = H, Z = F<br>A23: X = Cl, Y = H, Z = Cl<br>A24: X = Cl, Y = H, Z = H<br>A25: X = Br, Y = H, Z = H<br>A26: X = F, Y = F, Z = H<br>A27: X = NO2, Y = H, Z = H<br>A28: X = N(CH3)2, Y = H, Z = H<br>A29: X = F, Y = CF3, Z = H<br>A30: X = i-Pr, Y = H, Z = H<br>A31: X = 2-(5-F)-pyridine, Y = H, Z = H<br>C34: X = OPh(4-F), Y = H, Z = H |
| | C4: n = 1<br>C5: n = 2<br>C6: n = 3 |
| | C20: X = NO2, Y = H, Z = H<br>C21: X = NO2, Y = H, Z = NO2<br>C22: X = t-Bu, Y = H, Z = H<br>C23: X = Br, Y = H, Z = H<br>C24: X = OMe, Y = H, Z = H<br>C25: X = CF3, Y = CF3, Z = H<br>C26: X = F, Y = F, Z = H<br>C27: X = H, Y = CF3, Z = H<br>C28: X = H, Y = H, Z = Me<br>C29: X = H, Y = Me, Z = H<br>C30: X = Me, Y = H, Z = H |

TABLE 1-continued

| Compound structure. | Compound no., R = |
|---|---|
| | C31 |
| | A32 |
| | A33 |
| | A34 |
| | A35 |
| | A36 |
| | A37 |
| | A38 |

TABLE 1-continued

| Compound structure. | Compound no., R = |
|---|---|
| 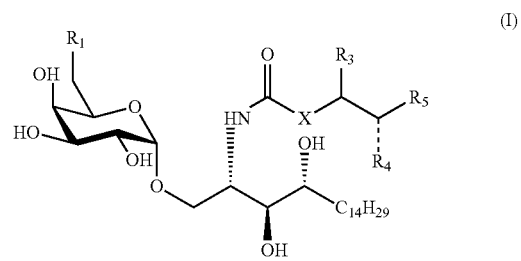 | A19, A20 |
| | A21 |
| | A39 |

Example 2

Antigen Presenting Cell (APC) Activation

Figure 6:
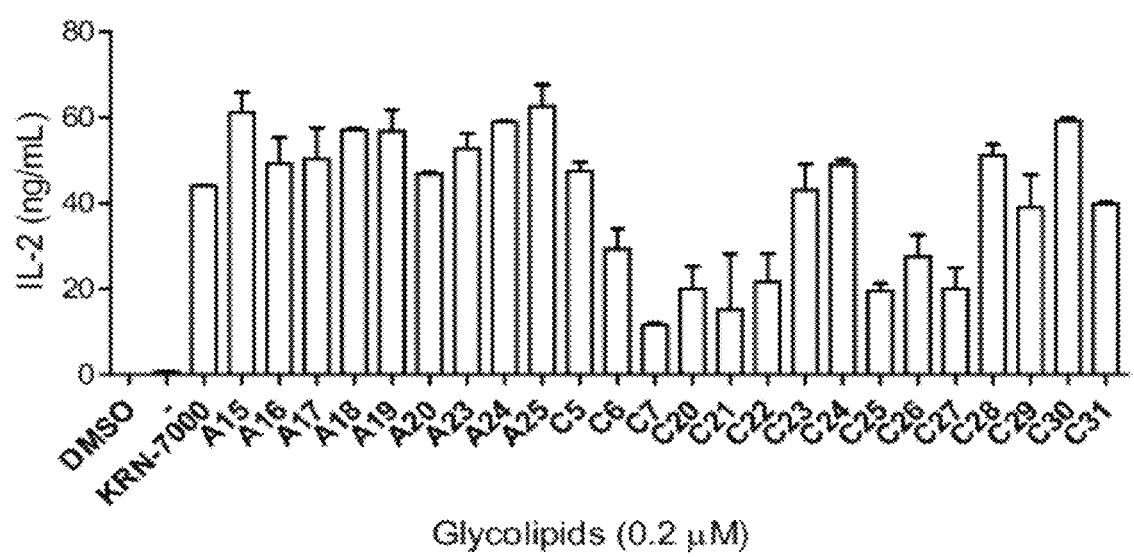
FIG. 6 shows glycosphingolipid-induced IL-2 secretion in A20CD1d and mNK1.2 cells system. Data are given as mean±SD; "-" indicates no compound.

A20CD1d cells and mNK1.2 cells were used as APC and effector cells, respectively. Guava ViaCount reagent was used to determine the viability and viable number of cells with Guava EasyCyte Plus. Mouse IL-2 DuoSet ELISA Development System was used to detect the production of IL-2. Cells and glycolipids were co-cultured at 37° C. and supernatant was collected at 24 h after culture. And, two days after culture, cells were harvested to determine the viability and the results show that these glycospingolipids are not toxic. As shown in FIG. 6, in this connection, all of test compounds exhibit APC activation activities.

IFN-γ and Il-4 Cytokine Secretions

Figure 7:
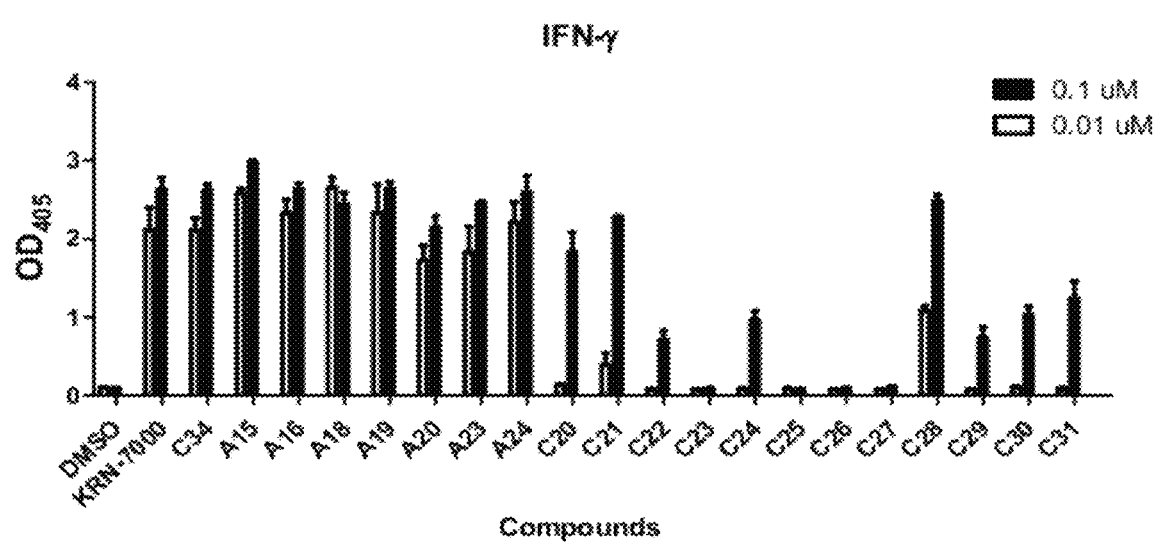
FIG. 7 shows INF-r cytokine secretion results by the splenocytes from female C57BL/6 mouse.
Figure 8:
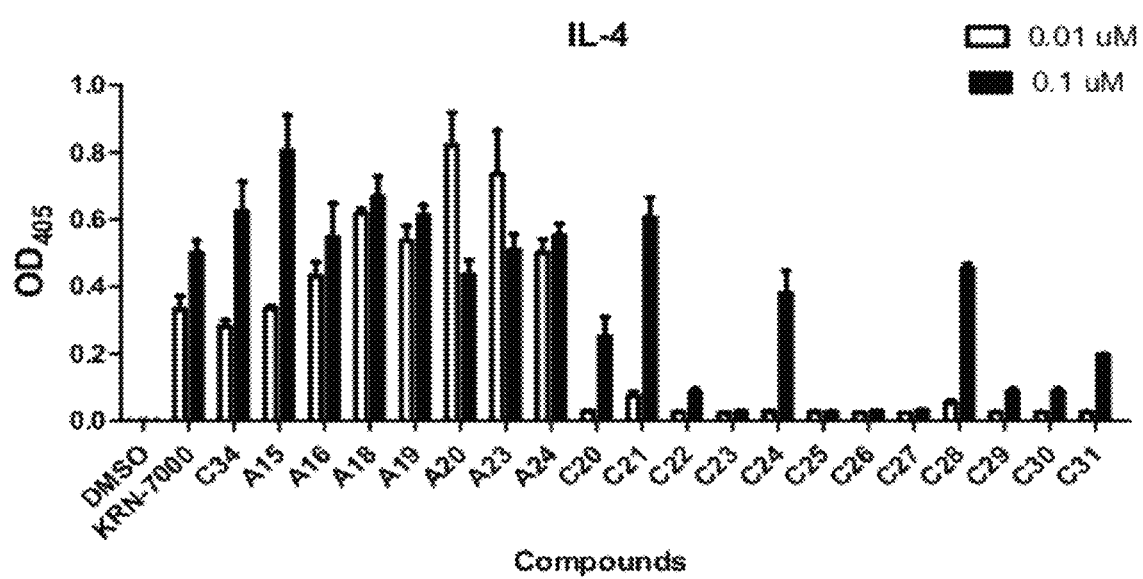
FIG. 8 shows IL-4 cytokine secretion results by the splenocytes from female C57BL/6 mouse.
Figure 9:
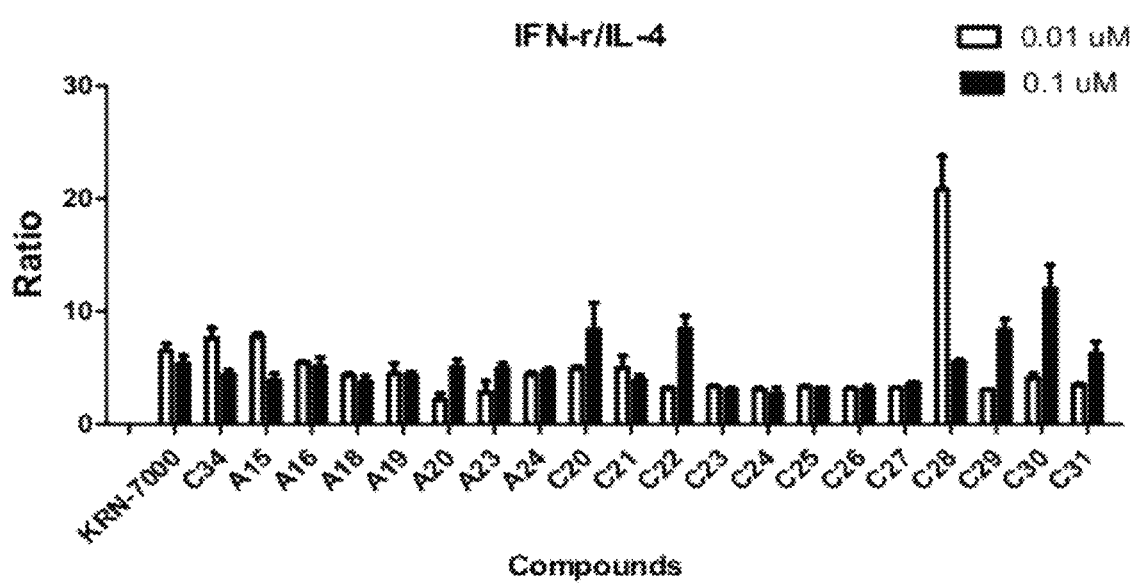
FIG. 9 shows cytokine secretion ratio which obtained from the comparison of FIGS. 7 & 8.

Female C57BL/6 mouse (16w4d) was sacrificed and spleen was harvested for the assay. Cells and glycolipids were coculture at 37° C. for 3 days and supernatant was collected at 3rd day (~60 h) after culture. Then, alarma Blue (5%/200 ul) was added and cells were cultured for 7 h to determine the cell proliferation. Mouse IL-4 and IFN-γ Duo Set ELISA Development System was used to detect the cytokine production. In this assay DMSO was negative control and KRN-7000 was positive control. As shown in the FIG. 7-9, compounds have shown Th1-biased cytokine secretion profile, indicating their applicability for antitumor, antiviral/antibacterial, and adjuvant activities.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. A process for preparing a chiral compound comprising an R-form or S-form of a glycosphingolipid of formula (1)

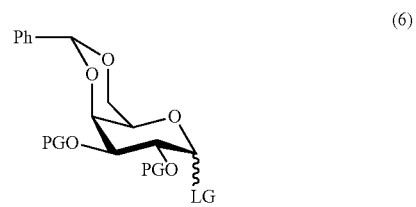

(I)

wherein $R_1$=OH, X=alkyl group, $R_3$=OH or H, $R_4$=OH or H, $R_5$=aryl, substituted aryl, heteroaryl, or substituted heteroaryl, or a pharmaceutically acceptable salt thereof, comprising the steps of (a) reacting by alpha-glycosylation in the presence of a Lewis acid and optionally, using molecular sieves to de-hydrate, a compound of formula (6):

(6)

wherein PG is a hydroxyl protecting group and LG is thio-toluene, with a compound represented by the structure of formula (7):

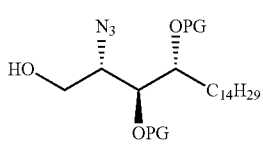

(7)

to obtain a compound of formula (5)

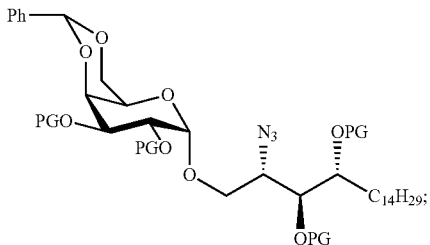

(5)

(b) reducing the compound of formula (5) to obtain a compound of formula (3)

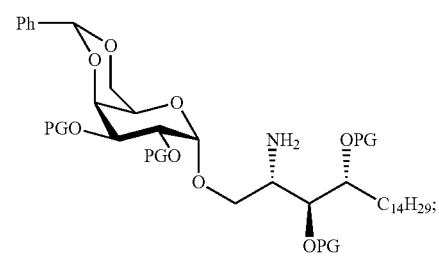

(3)

(c) coupling by the step of amide bond formation with coupling reagents, the compound of formula (3) with a compound of formula (4):

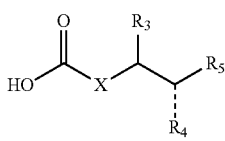

(4)

wherein X=alkyl group, alkenyl, $R_3$=H, OH, $R_4$=H, OH, $R_5$=aryl, substituted aryl, heteroaryl, or substituted heteroaryl, or a pharmaceutically acceptable salt thereof, to obtain a compound of formula (2):

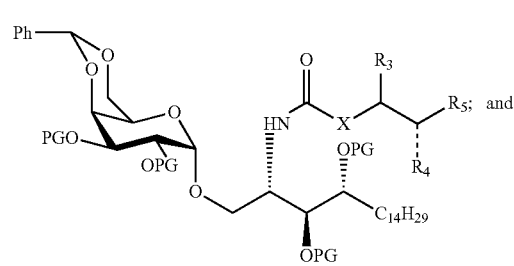

(2)

deprotecting the compound of formula (2) with hydrogen under hydrogenation catalysis to form the compound of formula (1).

2. The method of claim 1, wherein the hydrogenation catalyst is selected from Pd/C, Pd(OH$_2$), or Raney-Ni.

3. The method of claim 1, wherein the reduction is achieved using lithium aluminum hydride, sodium borohydride, a borane complex, enzyme reduction, hydrogenation, or transfer hydrogenation.

4. The method of claim 1, wherein the Lewis acid is selected from the group consisting of TMSOTf, Tf$_2$O, BF$_3$.OEt$_2$, TfOH, and Me$_2$S$_2$-Tf$_2$O.

5. The method of claim 1, wherein the compound of formula 1 is 1-O-(α-D-galactopyranosyl)-2-(11-(4-(4-fluorophenoxy)phenyl)undecanoyl)amino-D-ribo-octadecan-1,3,4-triol (C34) having the formula:

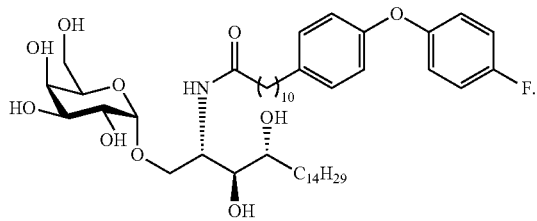

* * * * *